US009750722B2

(12) United States Patent
Chen et al.

(10) Patent No.: US 9,750,722 B2
(45) Date of Patent: Sep. 5, 2017

(54) DIAZOLE AMIDES

(71) Applicant: ChemoCentryx, Inc., Mountain View, CA (US)

(72) Inventors: Xi Chen, East Palo Alto, CA (US); Dean R. Dragoli, Los Altos, CA (US); Pingchen Fan, Fremont, CA (US); Juan C. Jaen, Burlingame, CA (US); Yandong Li, San Jose, CA (US); Jay P. Powers, Pacifica, CA (US); Viengkham Malathong, Belmont, CA (US); Sreenivas Punna, Sunnyvale, CA (US); Hiroko Tanaka, Foster City, CA (US); Penglie Zhang, Foster City, CA (US)

(73) Assignee: CHEMOCENTRYX, INC., Mountain View, CA (US)

( * ) Notice: Subject to any disclaimer, the term of this patent is extended or adjusted under 35 U.S.C. 154(b) by 0 days.

(21) Appl. No.: 14/878,784

(22) Filed: Oct. 8, 2015

(65) Prior Publication Data

US 2016/0193185 A1 Jul. 7, 2016

Related U.S. Application Data

(62) Division of application No. 14/137,479, filed on Dec. 20, 2013, now Pat. No. 9,169,248.

(60) Provisional application No. 61/745,444, filed on Dec. 21, 2012.

(51) Int. Cl.
*C07D 233/88* (2006.01)
*A61K 31/437* (2006.01)
*A61K 31/4178* (2006.01)
*A61K 45/06* (2006.01)
*C07D 401/12* (2006.01)
*A61K 31/4155* (2006.01)
*C07D 231/40* (2006.01)
*A61K 31/4192* (2006.01)
*A61K 31/4196* (2006.01)
*C07D 471/04* (2006.01)
*C07D 403/12* (2006.01)

(52) U.S. Cl.
CPC ...... *A61K 31/4155* (2013.01); *A61K 31/4178* (2013.01); *A61K 31/4192* (2013.01); *A61K 31/4196* (2013.01); *A61K 31/437* (2013.01); *A61K 45/06* (2013.01); *C07D 231/40* (2013.01); *C07D 233/88* (2013.01); *C07D 401/12* (2013.01); *C07D 403/12* (2013.01); *C07D 471/04* (2013.01)

(58) Field of Classification Search
CPC .. C07D 401/12; C07D 231/40; C07D 233/88; C07D 471/04; A61K 31/4196
USPC ...................... 548/312.7; 514/300
See application file for complete search history.

(56) References Cited

U.S. PATENT DOCUMENTS

| 5,817,677 A | 10/1998 | Linz et al. |
| 9,169,248 B2 | 10/2015 | Chen et al. |
| 2004/0192750 A1 | 9/2004 | Sanner et al. |
| 2006/0276428 A1 | 12/2006 | Elzein et al. |
| 2008/0004278 A1 | 1/2008 | Dyckman et al. |
| 2009/0143377 A1 | 6/2009 | Ng et al. |
| 2011/0230521 A1 | 9/2011 | Cook et al. |
| 2012/0108614 A1 | 5/2012 | Chong |
| 2014/0171420 A1 | 6/2014 | Chen et al. |

FOREIGN PATENT DOCUMENTS

| DE | 19539091 A1 | 4/1997 |
| EP | 1 319 657 A1 | 6/2003 |
| WO | 2008/045484 A1 | 4/2008 |
| WO | 2010/053861 A2 | 5/2010 |
| WO | 2011/029855 A1 | 3/2011 |

OTHER PUBLICATIONS

Gladue; Current Topics in Medicinal Chemistry 2010, 10, 1268-1277.*
Pease; J. Med. Chem. 2012, 55, 9363-9392.*
International Search Report and Written Opinion corresponding to PCT/US2013/077257 dated Jun. 25, 2014; 10 pages.
Ajuebor, Maureen N. et al., "Role of chemokines and chemokine receptors in the gastrointestinal tract," *Immunology* (2002; accepted Jul. 17, 2001); 105:137-143.
Anderson, Matthew W. et al., "C-C Chemokine Receptor 1 Expression in Human Hematolymphoid Nepolasia," *Am. J. Clin. Pathol.* (Mar. 1, 2010); 133(3):473-483.
Borregaard, Jeanett et al., "Evaluation of the effect of the specific CCR1 antagonist CP-481715 on the clinical and cellular responses observed following epicutaneous nickel challenge in human subjects," *Contact Dermatitis* (Feb. 18, 2008); 59:212-219.
Chemical Abstracts STN Record for CAS RN 1355557-26-4, entered Feb. 2, 2012.
Chemical Abstracts STN Record for CAS RN 1385289-59-7, entered Aug. 2, 2012.
Chemical Abstracts STN Record for CAS RN 1376355-87-1, entered Jun. 7, 2012.
Gao, Wei et al., "Targeting of the chemokine receptor CCR1 suppresses development of acute and chronic cardiac allograft rejection," *J. Clin. Invest.* (2000; accepted Nov. 23, 1999); 105(1):35-44.
Gladue, Ronald P., "Current status of CCR1 antagonists in clinical trials," *Chemokine Biology—Basic Research and Clinical Application*, vol. II (© 2007 Birkhäuser Verlag Basel/Switzerland); pp. 103-113.

(Continued)

Primary Examiner — Noble Jarrell
Assistant Examiner — Daniel Carcanague
(74) Attorney, Agent, or Firm — Mintz Levin Cohn Ferris Glovsky and Popeo PC

(57) ABSTRACT

Compounds are provided that act as potent antagonists of the CCR1 receptor, and have in vivo anti-inflammatory activity. The compounds are diazole lactam derivatives and are useful in pharmaceutical compositions, methods for the treatment of CCR1-mediated disease, and as controls in assays for the identification of competitive CCR1 antagonists.

23 Claims, No Drawings

(56) References Cited

OTHER PUBLICATIONS

Helal, Christopher J. et al., "Potent and cellularly active 4-aminoimidazole inhibitors of cyclin-dependent kinase 5/p25 for the treatment of Alzheimer's disease," *Bioorg. Med. Chem. Lett.* (Aug. 4, 2009); 19:5703-5707.
Hesselgesser, Joseph et al., "Identification and Characterization of Small Molecule Functional Antagonists of the CCR1 Chemokine Receptor," *J. Biol. Chem.* (Apr. 1, 1998); 273(25):15687-15692.
Joubert, Philippe et al., "Expression and Regulation of CCR1 by Airway Smooth Muscle Cells in Asthma," *J. Immunol.* (Feb. 1, 2008); 180:1268-1275.
Liang, Meina et al., "Species selectivity of a small molecule antagonist for the CCR1 chemokine receptor," *Eur. J. Pharmacol.* (2000; accepted Nov. 30, 1999); 389(1):41-49.
Liang, Meina et al., "Identification and Characterization of a Potent, Selective, and Orally Active Antagonist of the CC Chemokine Receptor-1," *J. Biol. Chem.* (Mar. 29, 2000); 275(25):19000-19008.
Ng, Howard P. et al., "Discovery of Novel Non-Peptide CCR1 Receptor Antagonists," *J. Med. Chem.* (Jun. 21, 1999); 42(22):4680-4694.
Rottman, James B. et al., "Leukocyte recruitment during onsent of experimental allergic encephalomyelitis is CCR1 dependent," *Eur. J. Immunol.* (May 15, 2000); 30:2372-2377.
Vallet S. et al., "CCR1 as a target for multiple myeloma," (Abstract, only) *Expert Opin. Ther. Targets* (Sep. 2011; Epub May 24, 2011); 15(9):1037-47.

\* cited by examiner

DIAZOLE AMIDES

CROSS-REFERENCES TO RELATED APPLICATIONS

This application claims the benefit of priority to U.S. Provisional application Ser. No. 61/745,444, filed Dec. 21, 2012, the entirety of which is incorporated herein by reference.

STATEMENT AS TO RIGHTS TO INVENTIONS MADE UNDER FEDERALLY SPONSORED RESEARCH AND DEVELOPMENT

Not Applicable

BACKGROUND OF THE INVENTION

The present invention provides compounds, pharmaceutical compositions containing one or more of those compounds or their pharmaceutically acceptable salts, which are effective in inhibiting the binding of various chemokines, such as MIP-1α, leukotactin, MPIF-1 and RANTES, to the CCR1 receptor. As antagonists or modulators for the CCR1 receptor, the compounds and compositions have utility in treating inflammatory and immune disorder conditions and diseases.

Human health depends on the body's ability to detect and destroy foreign pathogens that might otherwise take valuable resources from the individual and/or induce illness. The immune system, which comprises leukocytes (white blood cells (WBCs): T and B lymphocytes, monocytes, macrophages granulocytes, NK cell, mast cells, dendritic cell, and immune derived cells (for example, osteoclasts)), lymphoid tissues and lymphoid vessels, is the body's defense system. To combat infection, white blood cells circulate throughout the body to detect pathogens. Once a pathogen is detected, innate immune cells and cytotoxic T cells in particular are recruited to the infection site to destroy the pathogen. Chemokines act as molecular beacons for the recruitment and activation of immune cells, such as lymphocytes, monocytes and granulocytes, identifying sites where pathogens exist.

Despite the immune system's regulation of pathogens, certain inappropriate chemokine signaling can develop and has been attributed to triggering or sustaining inflammatory disorders, such as rheumatoid arthritis, multiple sclerosis and others. For example, in rheumatoid arthritis, unregulated chemokine accumulation in bone joints attracts and activates infiltrating macrophages and T-cells. The activities of these cells induce synovial cell proliferation that leads, at least in part, to inflammation and eventual bone and cartilage loss (see, DeVries, M. E., et al., Semin Immunol 11(2):95-104 (1999)). A hallmark of some demyelinating diseases such as multiple sclerosis is the chemokine-mediated monocyte/macrophage and T cell recruitment to the central nervous system (see, Kennedy, et al., J. Clin. Immunol. 19(5):273-279 (1999)). Chemokine recruitment of destructive WBCs to transplants has been implicated in their subsequent rejection. See, DeVries, M. E., et al., ibid. Because chemokines play pivotal roles in inflammation and lymphocyte development, the ability to specifically manipulate their activity has enormous impact on ameliorating and halting diseases that currently have no satisfactory treatment. In addition, transplant rejection may be minimized without the generalized and complicating effects of costly immunosuppressive pharmaceuticals.

Chemokines, a group of greater than 40 small peptides (7-10 kD), ligate receptors expressed primarily on WBCs or immune derived cells, and signal through G-protein-coupled signaling cascades to mediate their chemoattractant and chemostimulant functions. Receptors may bind more than one ligand; for example, the receptor CCR1 ligates RANTES (regulated on activation normal T cell expressed), MIP-1α (macrophage inflammatory protein), MPIF-1/CKβ8, and Leukotactin chemokines (among others with lesser affinities). To date, 24 chemokine receptors are known. The sheer number of chemokines, multiple ligand binding receptors, and different receptor profiles on immune cells allow for tightly controlled and specific immune responses. See, Rossi, et al., Ann. Rev. Immunol. 18(1):217-242 (2000). Chemokine activity can be controlled through the modulation of their corresponding receptors, treating related inflammatory and immunological diseases and enabling organ and tissue transplants.

The receptor CCR1 and its chemokine ligands, including, for example MIP-1α, MPIF-1/CKβ8, leukotactin and RANTES, represent significant therapeutic targets (see Saeki, et al., Current Pharmaceutical Design 9:1201-1208 (2003)) since they have been implicated in rheumatoid arthritis, transplant rejection (see, DeVries, M. E., et al., ibid.), and multiple sclerosis (see, Fischer, et al., J Neuroimmunol. 110(1-2):195-208 (2000); Izikson, et al., J. Exp. Med. 192(7):1075-1080 (2000); and Rottman, et al., Eur. J. Immunol. 30(8):2372-2377 (2000). In fact, function-blocking antibodies, modified chemokine receptor ligands and small organic compounds have been discovered, some of which have been successfully demonstrated to prevent or treat some chemokine-mediated diseases (reviewed in Rossi, et al., ibid.). Notably, in an experimental model of rheumatoid arthritis, disease development is diminished when a signaling-blocking, modified-RANTES ligand is administered (see Plater-Zyberk, et al., Immunol Lett. 57(1-3):117-120 (1997)). While function-blocking antibody and small peptide therapies are promising, they suffer from the perils of degradation, extremely short half-lives once administered, and prohibitive expense to develop and manufacture, characteristic of most proteins. Small organic compounds are preferable since they often have longer half lives in vivo, require fewer doses to be effective, can often be administered orally, and are consequently less expensive. Some organic antagonists of CCR1 have been previously described (see, Hesselgesser, et al., J. Biol. Chem. 273(25): 15687-15692 (1998); Ng, et al., J. Med. Chem. 42(22):4680-4694 (1999); Liang, et al., J. Biol. Chem. 275(25):19000-19008 (2000); and Liang, et al., Eur. J. Pharmacol. 389(1): 41-49 (2000)). In view of the effectiveness demonstrated for treatment of disease in animal models (see, Liang, et al., J. Biol. Chem. 275(25):19000-19008 (2000)), the search has continued to identify additional compounds that can be used in the treatment of diseases mediated by CCR1 signaling.

BRIEF SUMMARY OF THE INVENTION

The present invention relates to compounds having formula I:

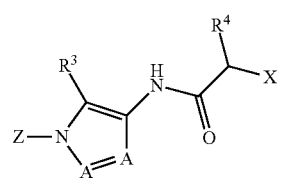

or a pharmaceutically acceptable salt, hydrate, solvate, N-oxide or rotamer thereof. In Formula I, each A is independently selected from the group consisting of N and CH; X and Z are each independently selected from the group consisting
  (i) monocyclic or fused-bicyclic aryl and heteroaryl, wherein the heteroaryl group has from 1-4 heteroatoms as ring members selected from N, O and S;
  (ii) monocyclic four-, five-, six- or seven-membered ring selected from the group consisting of cycloalkane, and heterocycloalkane, wherein the heterocycloalkane rings have from 1-3 heteroatoms as ring members selected from N, O and S;
  wherein each of the rings in (i) and (ii) are optionally substituted with from 1 to 5 substituents selected from halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —$OR^a$, —$CO_2R^a$, —$SO_2R^a$, —$NR^aR^b$, —$CONR^aR^b$, aryl, 5- or 6-membered heteroaryl, and 3-, 4-, 5- or 6-membered heterocycloalkane wherein the heteroatoms present as ring vertices of the heteroaryl and heterocycloalkane rings are selected from N, O and S, and wherein the alkyl, cycloalkyl, aryl, heteroaryl and hetereocycloalkane portions of the substituents are optionally further substituted with 1-3 $R^a$; and optionally, two substituents on adjacent ring vertices are connected to form an additional 5- or 6-membered ring which is saturated, unsaturated or aromatic having ring vertices selected from C, O, N and S;
  $R^3$ is a member selected from the group consisting of H, halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —$OR^a$, —$CO_2R^a$, —$NR^aR^b$, —$CONR^aR^b$, aryl, 5- or 6-membered heteroaryl, and 3-, 4-, 5- or 6-membered heterocyclic wherein the heteroatoms present as ring vertices of the heteroaryl and heterocyclic rings are selected from N, O and S, and wherein the alkyl, cycloalkyl, aryl, heteroaryl and hetereocyclic portions of $R^3$ are optionally further substituted with 1-3 $R^a$;
  $R^4$ is a member selected from the group consisting of H, —OR' and $C_{1-8}$ alkyl optionally substituted with —$OR^a$ or —$NR^aR^b$; or $R^4$ is combined with X to form a bicyclic fused ring system;
  each $R^a$ and $R^b$ is independently selected from the group consisting of hydrogen, hydroxyl, halogen, cyano, $C_{1-8}$ alkyl, $C_{1-8}$ alkoxy, $C_{1-8}$ haloalkyl, $C_{3-6}$ cycloalkyl, $C_{3-6}$ cycloalkylalkyl, amino, $C_{1-8}$ alkylamino, di $C_{1-8}$ alkylamino, carboxamide, carboxy $C_{1-4}$ alkyl ester, carboxylic acid, and —$SO_2$—$C_{1-8}$ alkyl.

In addition to the compounds provided herein, the present invention further provides pharmaceutical compositions containing one or more of these compounds, as well as methods for the use of these compounds primarily to treat diseases associated with CCR1 signalling activity.

BRIEF DESCRIPTION OF THE DRAWINGS

None

DETAILED DESCRIPTION OF THE INVENTION

I. Abbreviation and Definitions

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkane" or "heterocycloalkyl" refers to a cycloalkyl group that contains from one to five heteroatoms selected from N, O, and S, wherein the nitrogen and sulfur atoms are optionally oxidized, and the nitrogen atom(s) are optionally quaternized. The heterocycloalkane may be a monocyclic, a bicyclic or a polycylic ring system. Non limiting examples of heterocycloalkane groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkane group can be attached to the remainder of the molecule through a ring carbon or a heteroatom.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

As used herein, a wavy line, "$\sim\!\sim\!\sim$", that intersects a single, double or triple bond in any chemical structure depicted herein, represent the point attachment of the single, double, or triple bond to the remainder of the molecule.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or —$NR^aR^b$ is meant to include piperidinyl, pyrrolidinyl, morpholinyl, azetidinyl and the like.

The term "di-($C_{1-4}$alkyl)amino-$C_{1-4}$ alkyl" refers to an amino group bearing two $C_{1-4}$ alkyl groups that can be the same or different (e.g., methyl, ethyl, propyl, isopropyl, n-butyl, sec-butyl, isobutyl and tert-butyl) and which is attached to the remainder of the molecule through a $C_{1-4}$ alkyl group (a one to four carbon alkylene linking group). Examples of di-($C_{1-4}$ alkyl)amino-$C_{1-4}$ alkyl groups include dimethylaminomethyl, 2-(ethyl(methyl)amino)ethyl, 3-(dimethylamino)butyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

The term "arylalkyl" is meant to include those radicals in which an aryl group is attached to an alkyl group (e.g., benzyl, phenethyl, and the like). Similarly, the term "heteroaryl-alkyl" is meant to include those radicals in which a heteroaryl group is attached to an alkyl group (e.g., pyridylmethyl, thiazolylethyl, and the like).

The above terms (e.g., "alkyl," "aryl" and "heteroaryl"), in some embodiments, will refer to both substituted and unsubstituted forms of the indicated radical. Preferred substituents for each type of radical are provided below.

Substituents for the alkyl radicals (including those groups often referred to as alkylene, alkenyl, alkynyl and cycloalkyl) can be a variety of groups selected from: -halogen, —OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R'" each independently refer to hydrogen, unsubstituted $C_{1-8}$ alkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR' R", —NR'S(O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere with this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

Compounds of the invention having formula I can exist in different isomeric forms. As used herein, the terms cis or trans are used in their conventional sense in the chemical arts, i.e., referring to the position of the substituents to one another relative to a reference plane, e.g., a double bond, or a ring system, such as a decalin-type ring system or a hydroquinolone ring system: in the cis isomer, the substituents are on the same side of the reference plane, in the trans isomer the substituents are on opposite sides. Additionally, different conformers are contemplated by the present invention, as well as distinct rotamers. Conformers are conformational isomers that can differ by rotations about one or more σ bonds. Rotamers are conformers that differ by rotation about only a single σ bond.

II. General

The present invention derives from the discovery that compounds of formula I act as potent antagonists of the CCR1 receptor. The compounds have in vivo anti-inflammatory activity and have superior pharmacokinetic properties. Accordingly, the compounds provided herein are useful in pharmaceutical compositions, methods for the treatment of CCR1-mediated diseases, and as controls in assays for the identification of competitive CCR1 antagonists.

III. Compounds

In one aspect, the present invention provides for a compound of Formula I:

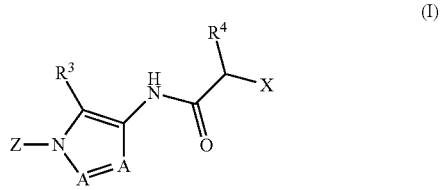

or pharmaceutically acceptable salt, hydrate, solvate, N-oxide or rotamer thereof. In Formula I, each A is independently selected from the group consisting of N and CH;

X and Z are each independently selected from the group consisting
- (i) monocyclic or fused-bicyclic aryl and heteroaryl, wherein the heteroaryl group has from 1-4 heteroatoms as ring members selected from N, O and S;
- (ii) monocyclic four-, five-, six- or seven-membered ring selected from the group consisting of cycloalkane, and heterocycloalkane, wherein the heterocycloalkane rings have from 1-3 heteroatoms as ring members selected from N, O and S;
- wherein each of the rings in (i) and (ii) are optionally substituted with from 1 to 5 substituents selected from halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —OR$^a$, —CO$_2$R$^a$, —SO$_2$R$^a$, —NR$^a$R$^b$, —CONR$^a$R$^b$, aryl, 5- or 6-membered heteroaryl, and 3-, 4-, 5- or 6-membered heterocycloalkane wherein the heteroatoms present as ring vertices of the heteroaryl and heterocycloalkane rings are selected from N, O and S, and wherein the alkyl, cycloalkyl, aryl, heteroaryl and hetereocycloalkane portions of the substituents are optionally further substituted with 1-3 $R^a$; and optionally, two substituents on adjacent ring vertices are connected to form an additional 5- or 6-membered ring which is saturated, unsaturated or aromatic having ring vertices selected from C, O, N and S;

$R^3$ is a member selected from the group consisting of H, halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —$OR^a$, —$CO_2R^a$, —$NR^aR^b$, —$CONR^aR^b$, aryl, 5- or 6-membered heteroaryl, and 3-, 4-, 5- or 6-membered heterocyclic wherein the heteroatoms present as ring vertices of the heteroaryl and heterocyclic rings are selected from N, O and S, and wherein the alkyl, cycloalkyl, aryl, heteroaryl and heterocyclic portions of $R^3$ are optionally further substituted with 1-3 $R^a$;

$R^4$ is a member selected from the group consisting of H, —$OR^a$ and $C_{1-8}$ alkyl optionally substituted with —$OR^a$ or —$NR^aR^b$; or $R^4$ is combined with X to form a bicyclic fused ring system; and each $R^a$ and $R^b$ is independently selected from the group consisting of hydrogen, hydroxyl, halogen, cyano, $C_{1-8}$ alkyl, $C_{1-8}$ alkoxy, $C_{1-8}$ haloalkyl, $C_{3-6}$ cycloalkyl, $C_{3-6}$ cycloalkylalkyl, amino, $C_{1-8}$ alkylamino, di $C_{1-8}$ alkylamino, carboxamide, carboxy $C_{1-4}$ alkyl ester, carboxylic acid, and —$SO_2$—$C_{1-8}$ alkyl.

One of skill in the art will appreciate that substituent recitations only refer to those that are generally stable (e.g., less than 20% degradation on storage), such that the group —$OR^a$ is not meant to include those components wherein $R^a$ is alkoxy (which would furnish a peroxy or —OO-alkyl group).

In some selected embodiments, the compounds of Formula I are represented by Formula Ia:

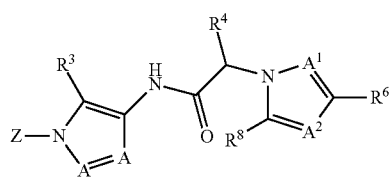

(Ia)

wherein $A^1$ is N or $C(R^5)$; $A^2$ is N or $C(R^7)$; and $R^5$, $R^6$, $R^7$ and $R^8$ are each independently selected from H, halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —$OR^a$, —$CO_2R^a$, —$NR^aR^b$, —$CONR^aR^b$, aryl, 5- or 6-membered heteroaryl, and 3-, 4-, 5- or 6-membered heterocycloalkane wherein the heteroatoms present as ring vertices of the heteroaryl and heterocycloalkane rings are selected from N, O and S, and wherein the alkyl, cycloalkyl, aryl, heteroaryl and heterocycloalkane portions of $R^5$, $R^6$, $R^7$ and $R^8$ are optionally further substituted with 1-3 $R^a$; and optionally, and optionally, $R^4$ and $R^5$, $R^4$ and $R^8$, or adjacent members of $R^5$, $R^6$, $R^7$ and $R^8$ are connected to form an additional 5- or 6-membered ring which is saturated, unsaturated or aromatic having ring vertices selected from C, O, N and S; or a pharmaceutically acceptable salt, hydrate, solvate, rotamer or N-oxide thereof.

In other selected embodiments, the compounds of Formula Ia are those wherein $R^8$ is other than H.

In other selected embodiments, the compounds of Formula Ia are represented by Formula Ib:

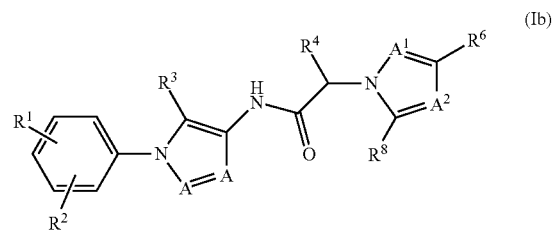

(Ib)

wherein $R^1$ and $R^2$ are each independently selected from H, halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —$OR^a$, —$CO_2R^a$, —$SO_2R^a$, —$NR^aR^b$, —$CONR^aR^b$, and 3-, 4-, 5- or 6-membered heterocycloalkane wherein the heteroatoms present as ring vertices of the heterocycloalkane ring are selected from N, O and S, and wherein the alkyl, cycloalkyl and hetereocycloalkane portions of $R^1$ and $R^2$ are optionally further substituted with 1-3 $R^a$.

In selected embodiments of Formula Ib, each $R^1$ and $R^2$ is independently selected from H, halogen, CN, $C_{1-8}$ alkyl, $C_{1-8}$ haloalkyl, —$CO_2R^a$ and —$SO_2R^a$.

In other selected embodiments for the compounds of Formula Ib, the compounds are represented by the structure:

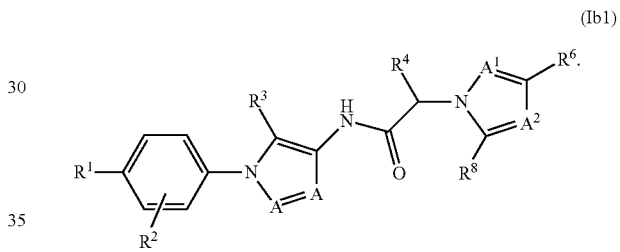

(Ib1)

In other selected embodiments for the compounds of Formula Ib and Ib1, the ring portion having N, $A^1$ and $A^2$ as ring vertices is selected from:

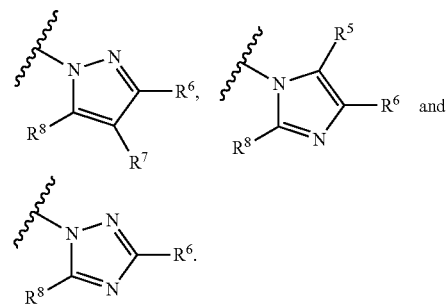

and

In still other selected embodiments for the compounds of Formula Ib and Ib1, the ring portion having N, $A^1$ and $A^2$ as ring vertices is selected from:

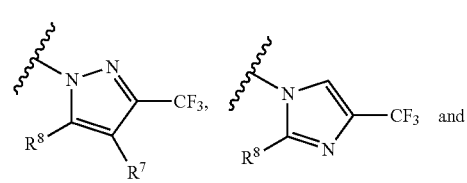

and

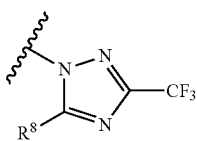

wherein $R^7$ is H or Cl, and $R^8$ is $C_{1-8}$ alkyl optionally substituted with 1 or 2 $R^a$.

In still other selected embodiments of Formula Ib or Ib1, $R^4$ is H or $CH_3$.

Returning to Formula I, some selected embodiments are those compounds represented by Formula Ib2:

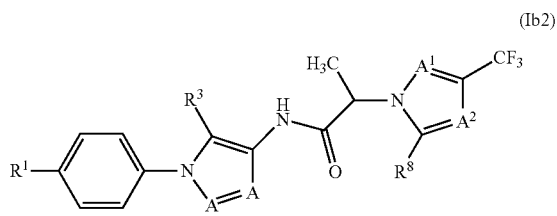

wherein $R^1$ is Cl or F; $R^3$ is selected from the group consisting of $C_{1-8}$ alkyl, $C_{1-8}$ haloalkyl, $C_{1-8}$ hydroxyalkyl, wherein the alkyl portions of $R^3$ are optionally further substituted with 1-3 $R^a$; and wherein $R^7$ and $R^8$ are not joined to form a ring In still other selected embodiments, the compounds of Formula I, Ib, Ib1 and Ib2 are represented by Formulae Ib2a, Ib2b and Ib2c.

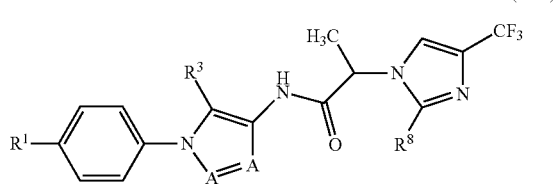

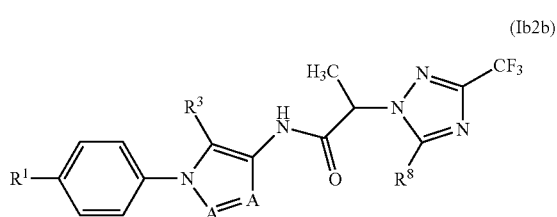

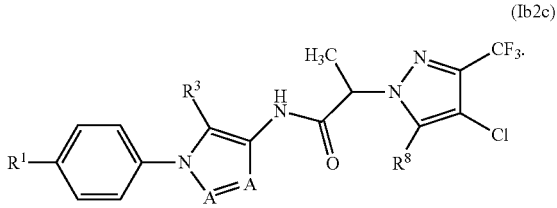

In some selected embodiments, the compounds are represented by Formula Ic:

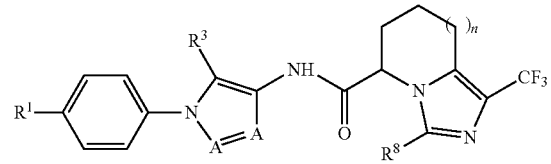

wherein the subscript n is 0 or 1.

In some selected embodiments, the compounds are represented by Formula Ib3:

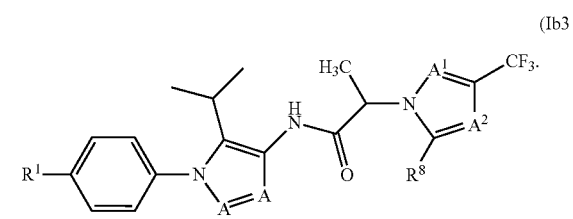

In some selected embodiments of Formula Ib, the compounds are represented by Formulae Ib2d, Ib2e and Ib2f.

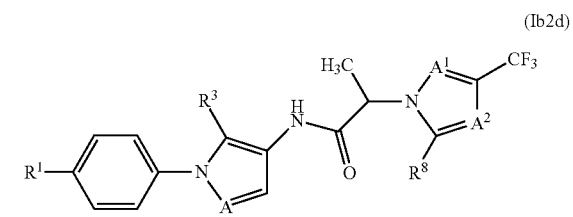

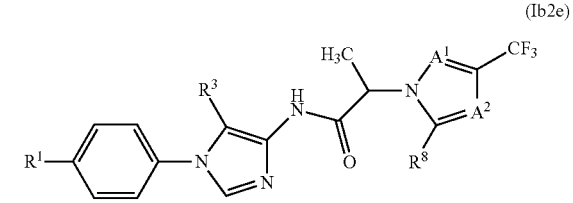

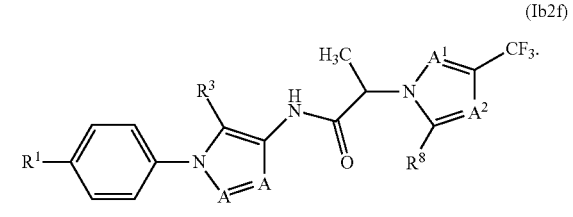

In selected embodiments of any of Formulae I, Ia, Ib, Ib1, Ib2, Ib2a, Ib2b, Ib2c, Ib2d, Ib2e, Ib2f, Ib3 and Ic, $R^3$ is $C_{1-8}$ alkyl.

Preparation of Compounds

The schemes in the Examples below provide certain synthetic routes that can be followed to access certain compounds of the present invention. Other routes or modification of the routes presented below would be readily apparent to a skilled artisan and are within the scope of the present invention.

IV. Pharmaceutical Compositions

In addition the compounds provided above, the compositions for modulating CCR1 activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Pat. No. 6,451,339, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of the invention may be formulated for depositing into a medical device, which may include any of variety of conventional grafts, stents, including stent grafts, catheters, balloons, baskets or other device that can be deployed or permanently implanted within a body lumen. As a particular example, it would be desirable to have devices and methods which can deliver compounds of the invention to the region of a body which has been treated by interventional technique.

In exemplary embodiment, the inhibitory agent of this invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also used to deliver a drug at the site of contact with the vasculature, as disclosed in U.S. Pat. No. 5,102,417 (Palmaz) and in International Patent Application Nos. WO 91/12779 (Medtronic, Inc.) and WO 90/13332 (Cedars-Sanai Medical Center), U.S. Pat. No. 5,419,760 (Narciso, Jr.) and U.S. Pat. No. 5,429,634 (Narciso, Jr.), for example. Stents have also been used to deliver viruses to the wall of a lumen for gene delivery, as disclosed in U.S. Pat. No. 5,833,651 (Donovan et al.).

The term "deposited" means that the inhibitory agent is coated, adsorbed, placed, or otherwise incorporated into the device by methods known in the art. For example, the inhibitory agent may be embedded and released from within ("matrix type") or surrounded by and released through ("reservoir type") polymer materials that coat or span the medical device. In the later example, the inhibitory agent may be entrapped within the polymer materials or coupled to the polymer materials using one or more the techniques for generating such materials known in the art. In other formulations, the inhibitory agent may be linked to the surface of the medical device without the need for a coating by means of detachable bonds and release with time, can be removed by active mechanical or chemical processes, or are in a permanently immobilized form that presents the inhibitory agent at the implantation site.

In one embodiment, the inhibitory agent may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D,L-lactic acid), poly(D,L-lactide) (PLA), poly (L-lactide) (PLLA), poly(glycolic acid-co-trimethylene carbonate) (PGA/PTMC), polyethylene oxide (PEO), polydioxanone (PDS), polyphosphoester, polyphosphoester urethane, poly (amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable poplymers known in the art. Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In one embodiment of the invention, the inhibitory agent of the invention is coupled to a polymer or semipermeable polymer matrix that is formed as a stent or stent-graft device.

Typically, polymers are applied to the surface of an implantable device by spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In preferred embodiments of the invention, the inhibitory agent is formulated for release from the polymer coating into the environment in which the medical device is placed. Preferably, the inhibitory agent is released in a controlled manner over an extended time frame (e.g., months) using at least one of several well-known techniques involving polymer carriers or layers to control elution. Some of these techniques were previously described in U.S. Patent Application 20040243225A1.

Moreover, as described for example in U.S. Pat. No. 6,770,729, the reagents and reaction conditions of the polymer compositions can be manipulated so that the release of the inhibitory agent from the polymer coating can be controlled. For example, the diffusion coefficient of the one or more polymer coatings can be modulated to control the release of the inhibitory agent from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the inhibitory agent from the polymer coating). Yet another embodiment of the invention includes a device having a plurality of polymer coatings, each having a plurality of diffusion coefficients. In such embodiments of the invention, the release of the inhibitory agent from the polymer coating can be modulated by the plurality of polymer coatings.

In yet another embodiment of the invention, the release of the inhibitory agent from the polymer coating is controlled by modulating one or more of the properties of the polymer composition, such as the presence of one or more endogenous or exogenous compounds, or alternatively, the pH of the polymer composition. For example, certain polymer compositions can be designed to release a inhibitory agent in response to a decrease in the pH of the polymer composition. Alternatively, certain polymer compositions can be designed to release the inhibitory agent in response to the presence of hydrogen peroxide.

III. Methods of Treating Diseases Modulated by CCR1

In yet another aspect, the present invention provides methods of treating CCR1-mediated conditions or diseases by administering to a subject having such a disease or condition, a therapeutically effective amount of a compound of formula I above. The "subject" is defined herein to include animals such as mammals, including, but not limited to, primates (e.g., humans), cows, sheep, goats, horses, dogs, cats, rabbits, rats, mice and the like.

CCR1 provides a target for interfering with or promoting specific aspects of immune cell functions, or more generally, with functions associated with CCR1 expression on a wide range of cell types in a mammal, such as a human. Compounds that inhibit CCR1, are particularly useful for modulating monocyte, macrophage, lymphocyte, granulocyte, NK cell, mast cells, dendritic cell, and certain immune derived cell (for example, osteoclasts) function for therapeutic purposes. Accordingly, the present invention is directed to compounds which are useful in the prevention and/or treatment of a wide variety of inflammatory and immunoregulatory disorders and diseases (see Saeki, et al., *Current Pharmaceutical Design* 9:1201-1208 (2003)).

For example, an instant compound that inhibits one or more functions of CCR1 may be administered to inhibit (i.e., reduce or prevent) inflammation or cellular infiltration associated with an immune disorder. As a result, one or more inflammatory processes, such as leukocyte emigration or infiltration, chemotaxis, exocytosis (e.g., of enzymes, histamine) or inflammatory mediator release, can be inhibited. For example, monocyte infiltration to an inflammatory site (e.g., an affected joint in arthritis, or into the CNS in MS) can be inhibited according to the present method.

Similarly, an instant compound that promotes one or more functions of CCR1 is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, monocytes can be recruited to combat bacterial infections.

Diseases and conditions associated with inflammation, immune disorders and infection can be treated using the method of the present invention. In a preferred embodiment, the disease or condition is one in which the actions of immune cells such monocyte, macrophage, lymphocyte, granulocyte, NK cell, mast cell, dendritic cell, or certain immune derived cell (for example, osteoclasts) are to be inhibited or promoted, in order to modulate the inflammatory or autoimmune response.

In one group of embodiments, diseases or conditions, including chronic diseases, of humans or other species can treated with modulators of CCR1 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as asthma, allergic asthma, allergic rhinitis, hypersensitivity lung diseases and the like, (9) autoimmune diseases, such as fibromyalagia, scleroderma, ankylosing spondylitis, juvenile RA, Still's disease, polyarticular juvenile RA, pauciarticular juvenile RA, polymyalgia rheumatica, Takuyasu arthritis, rheumatoid arthritis, psoriatic arthritis, osteoarthritis, polyarticular arthritis, multiple sclerosis, systemic lupus erythematosus, type I diabetes, type II diabetes, type I diabetes (recent onset), optic neuritis, glomerulonephritis, and the like, (10) graft rejection including allograft rejection and acute and chronic graft-vs-host disease, (11) fibrosis (e.g. pulmonary fibrosis (i.e. idiopathic pulmonary fibrosis, interstitial pulmonary fibrosis), fibrosis associated with end-stage renal disease, fibrosis caused by radiation, tubulointerstitial fibrosis, subepithelieal fibrosis, scleroderma (progressive systemic sclerosis), hepatic fibrosis (including that caused by alcoholic or viral hepatitis), primary and secondary cirrhosis), (12) acute and chronic lung inflammation (chronic obstructive pulmonary disease, chronic bronchitis, adult respiratory distress syndrome, respiratory distress syndrome of infancy, immune complex alveolitis) and (13) other diseases in which undesired inflammatory responses or immune disorders are to be inhibited, such as cardiovascular disease including atherosclerosis, vascular inflammation resulting from tissue transplant or during restenosis (including, but not limited to restenosis following angioplasty and/or stent insertion), other acute and chronic inflammatory conditions such as myositis, neurodegenerative diseases (e.g., Alzheimer's disease), encephalitis, meningitis, hepatitis, nephritis, sepsis, sarcoidosis, allergic conjunctivitis, otitis, sinusitis, synovial inflammation caused by arthroscopy, hyperuremia, trauma, ischaemia reperfusion injury, nasal polyosis, preeclampsia, oral lichen planus, Guillina-Barre syndrome, granulomatous diseases, conditions associated with leptin production, Behcet's syndrome and gout and in wound healing applications (14) immune mediated food allergies such as Celiac disease (15) diseases of osteoclast dysregulation including osteoporosis and osteolytic bone diseases associated with cancers such as multiple myeloma.

In another group of embodiments, diseases or conditions can be treated with modulators of CCR1 function. Examples of diseases to be treated with modulators of CCR1 function include cancers (both primary and metastatic) (e.g., multiple myeloma; Hata, H., Leukemia & Lymphoma, 2005, 46(7); 967-972), cardiovascular diseases, diseases in which angiogenesis or neovascularization play a role (neoplastic diseases, retinopathy and macular degeneration), infectious diseases (viral infections, e.g., HIV infection, and bacterial infections) and immunosuppressive diseases such as organ transplant conditions and skin transplant conditions. The term "organ transplant conditions" is meant to include bone marrow transplant conditions and solid organ (e.g., kidney, liver, lung, heart, pancreas or combination thereof) transplant conditions.

Pharmaceutical compositions of this invention can also inhibit the production of metalloproteinases and cytokines at inflammatory sites, either directly or indirectly (as a consequence of decreasing cell infiltration) thus providing benefit for diseases or conditions linked to these cytokines.

The compounds of the present invention are accordingly useful in the prevention and treatment of a wide variety of inflammatory and immunoregulatory disorders and diseases.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

Those of skill in the art will understand that agents that modulate CCR1 activity can be combined in treatment regimens with other therapeutic agents and/or with chemotherapeutic agents or radiation. In some cases, the amount of chemotherapeutic agent or radiation is an amount which would be sub-therapeutic if provided without combination with a composition of the invention. Those of skill in the art will appreciate that "combinations" can involve combinations in treatments (i.e., two or more drugs can be administered as a mixture, or at least concurrently or at least introduced into a subject at different times but such that both are in the bloodstream of a subject at the same time). Additionally, compositions of the current invention may be administered prior to or subsequent to a second therapeutic regimen, for instance prior to or subsequent to a dose of chemotherapy or irradiation.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

Diseases and conditions associated with inflammation, immune disorder, infection and cancer can be treated or prevented with the present compounds, compositions, and methods.

The compounds and compositions of the present invention can be combined with other compounds and compositions having related utilities to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autoimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

Likewise, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolirnus (FK-506, Prograf®), rapamycin (sirolimus, Rapamune®), Tofacitinib (Xeljanz®) and other FK-506 type immunosuppressants, and mycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106,203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, niroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), adalimumab (Humira®), golimumab (Simponi®), rituximab (Rituxan®), tocilizumab (Actemra®), (l) other antagonists of the chemokine receptors, especially CCR5, CXCR2, CXCR3, CCR2, CCR3, CCR4, CCR7, $CX_3CR1$ and CXCR6; (m) lubricants or emollients such as petrolatum and lanolin, (n) keratolytic agents (e.g., tazarotene), (o) vitamin $D_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α (Avonex®), azathioprine (Imurek®, Imuran®), glatiramer acetate (Capoxone®), a glucocorticoid (e.g., prednisolone) and cyclophosphamide (t) DMARDS such as methotrexate and leflunomide (u) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydmxyurea and microtubule disrupters such as colchicine and proteasome inhibitors such as bortezomib (Velcade®). The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

IV. Examples

The following examples are offered to illustrate, but not to limit the claimed invention.

Reagents and solvents used below can be obtained from commercial sources such as Aldrich Chemical Co. (Milwaukee, Wis., USA). $^1$H-NMR were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In tables, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC equipped with an Agilent Zorbax SB-C18, 2.1×50 mm, 5μ column for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as delivery system.

The following abbreviations are used in the Examples and throughout the description of the invention:

HPLC, High Pressure Liquid Chromatography; DMF, Dimethyl formamide; TFA, Trifluoroacetic Acid; THF, Tetrahydrofuran; EtOAc, Ethyl acetate; BOC$_2$O, di-tertbutyl dicarbonate or BOC anhydride; HPLC, High Pressure Liquid Chromatography; DIPEA, Diisopropyl ethylamine; HBTU, O-(benzotriazol-1-yl)-N,N,N',N'-tetramethyluronium hexafluorophosphate; dppf, 1,1'-Bis(diphenylphosphino)ferrocene; Pd$_2$(dba)$_3$, Tris(dibenzylideneacetone)dipalladium (0); DIPEA, diisopropylethylamine; DMP, dimethylphthalate; Me, methyl; Et, ethyl; DCM, dichloromethane.

Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Examples

Example 1

Synthesis of 2-[4-chloro-5-methyl-3-(trifluoromethyl)pyrazol-1-yl]-N-[1-(4-fluorophenyl)-5-methyl-pyrazol-4-yl]acetamide

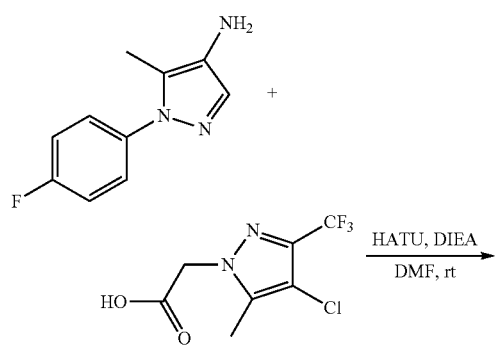

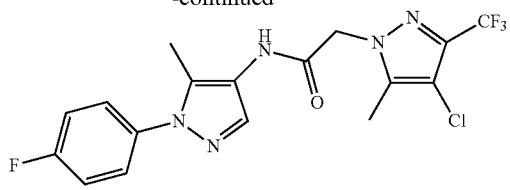

To a solution of 1-(4-fluorophenyl)-5-isopropylpyrazol-4-amine (0.03 g, 0.16 mmol) in DMF (1.0 mL) was added 2-[4-chloro-5-methyl-3-(trifluoromethyl)pyrazol-1-yl]acetic acid (0.038 g, 0.16 mmol), followed by diisopropylethylamine (0.042 g, 0.32 mmol) and HATU (0.067 g, 0.18 mmol). After stirring at room temperature for 1 h, the reaction was diluted with water and the aqueous layer was extracted with ethyl acetate (2×5 mL). The combined organic layers were washed with brine, dried (Na$_2$SO$_4$), filtered, and concentrated in vacuo. The resulting crude product was purified by reverse phase HPLC (C18 column, acetonitrile-H$_2$O with 0.1% TFA as eluent) to give the title compound as a white solid (0.02 g, 0.048 mmol, 30%). $^1$H NMR (400 MHz, CDCl$_3$) δ 7.93 (s, 1H), 7.37 (dd, J=8.9, 4.7 Hz, 1H), 7.26 (d, J=0.4 Hz, 2H), 7.18 (dd, J=8.9, 8.1 Hz, 2H), 4.94 (s, 2H), 2.39 (s, 3H), 2.16 (s, 3H); MS: (ES) m/z calculated for C$_{17}$H$_{14}$ClF$_4$N$_5$O [M+H]$^+$ 416.1, found 416.0.

Example 2

Synthesis of N-[1-(4-fluorophenyl)-5-methylpyrazol-4-yl]-2-[2-methyl-4-(trifluoromethyl)imidazol-1-yl]propanamide

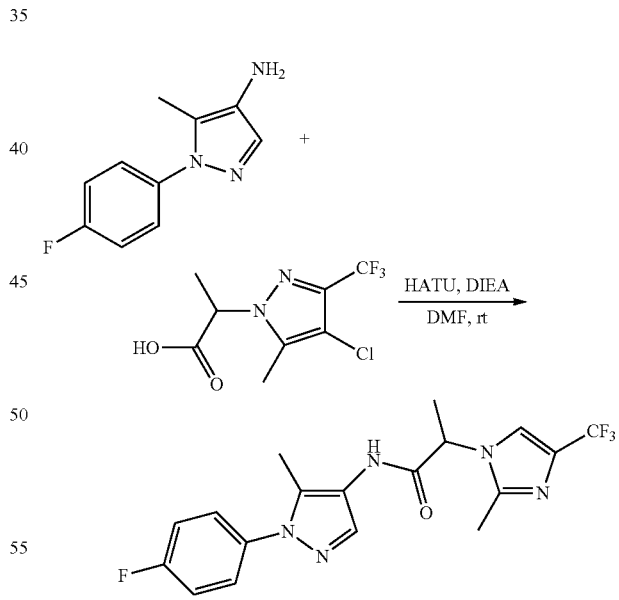

To a solution of 1-(4-fluorophenyl)-5-methylpyrazol-4-amine (0.03 g, 0.16 mmol) in DMF (1.0 mL) was added 2-[2-methyl-4-(trifluoromethyl)imidazol-1-yl]propanoic acid (0.035 g, 0.16 mmol), followed by diisopropylethylamine (0.042 g, 0.32 mmol) and HATU (0.067 g, 0.18 mmol). After stirring at room temperature for 1 h, the reaction was diluted with water, and the aqueous layer was extracted with ethyl acetate (2×5 mL). The combined organic layers were washed with brine, dried (Na$_2$SO$_4$), filtered, and concentrated in vacuo. The resulting crude product was purified by reverse phase HPLC (C18 column, acetonitrile-H$_2$O with 0.1% TFA as eluent) to give the title compound as a white solid (0.015 g, 0.038 mmol, 24%). $^1$H NMR (400 MHz, CDCl$_3$) δ 8.93 (s, 1H), 7.93 (s, 1H), 7.81 (d, J=1.3 Hz, 1H), 7.42-7.32 (m, 2H), 7.24-7.14 (m, 2H), 5.35 (q, J=6.8 Hz, 1H), 2.48 (s, 3H), 2.19 (s, 3H), 1.86 (d, J=7.0 Hz, 3H); MS: (ES) m/z calculated for C$_{18}$H$_{17}$F$_4$N$_5$O [M+H]$^+$ 396.1, found 396.1.

Example 3

Synthesis of 2-[4-chloro-5-methyl-3-(trifluoromethyl)pyrazol-1-yl]-N-[5-ethyl-1-(4-fluorophenyl)pyrazol-4-yl]acetamide

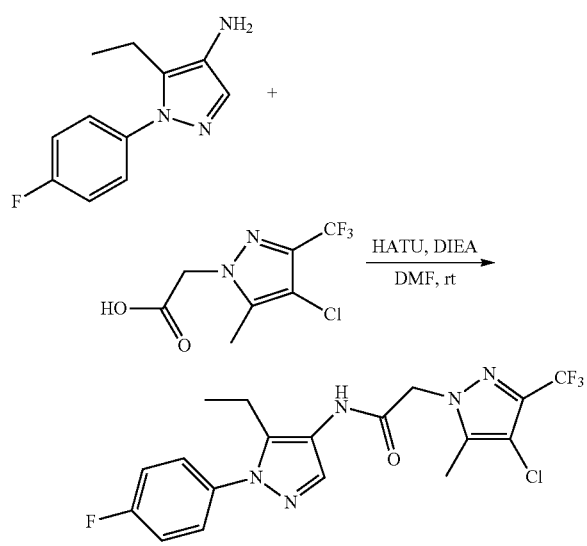

To a solution of 5-ethyl-1-(4-fluorophenyl)pyrazol-4-amine (0.02 g, 0.1 mmol) in DMF (1.0 mL) was added 2-[4-chloro-5-methyl-3-(trifluoromethyl)pyrazol-1-yl]acetic acid (0.024 g, 0.10 mmol), followed by diisopropylethylamine (0.042 g, 0.32 mmol) and HATU (0.045 g, 0.12 mmol). After stirring at room temperature for 1 h, the reaction was diluted with water, and the aqueous layer was extracted with ethyl acetate (2×5 mL). The combined organic layers were washed with brine, dried (Na$_2$SO$_4$), filtered, and concentrated in vacuo. The resulting crude product was purified by reverse phase HPLC (C18 column, acetonitrile-H$_2$O with 0.1% TFA as eluent) to give the title compound as a white solid (0.015 g, 0.035 mmol, 35%). $^1$H NMR (400 MHz, CDCl$_3$) δ 7.97 (s, 1H), 7.92 (s, 1H), 7.40-7.31 (m, 2H), 7.17 (dd, J=8.9, 8.1 Hz, 2H), 4.93 (s, 2H), 2.56 (q, J=7.6 Hz, 2H), 2.39 (s, 3H), 1.01 (t, J=7.6 Hz, 3H); MS: (ES) m/z calculated for C$_{18}$H$_{16}$ClF$_4$N$_5$O [M+H]$^+$ 430.1, found 430.0.

Example 4

Synthesis of 2-[4-chloro-5-methyl-3-(trifluoromethyl)pyrazol-1-yl]-N-[1-(4-fluorophenyl)-5-isopropylpyrazol-4-yl]acetamide

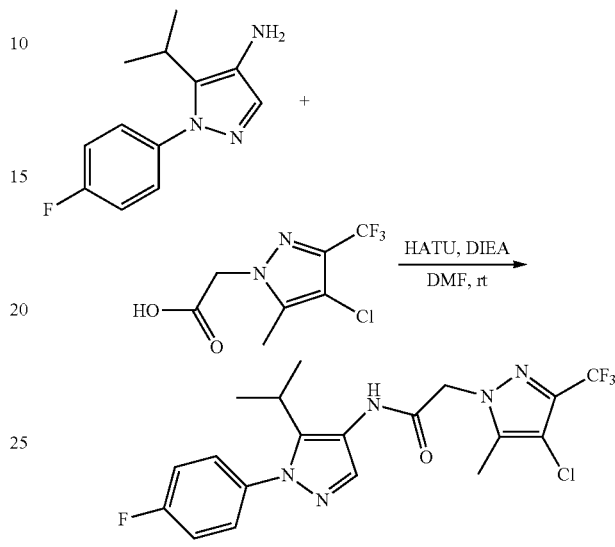

To a solution of 1-(4-fluorophenyl)-5-isopropylpyrazol-4-amine (0.035 g, 0.16 mmol) in DMF (1.0 mL) was added 2-[4-chloro-5-methyl-3-(trifluoromethyl)pyrazol-1-yl]acetic acid (0.039 g, 0.16 mmol), followed by diisopropylethylamine (0.042 g, 0.32 mmol) and HATU (0.073 g, 0.19 mmol). After stirring at room temperature for 1 h, the reaction was diluted with water, and the aqueous layer was extracted with ethyl acetate (2×5 mL). The combined organic layers were washed with brine, dried (Na$_2$SO$_4$), filtered, and concentrated in vacuo. The resulting crude product was purified by reverse phase HPLC (C18 column, acetonitrile-H$_2$O with 0.1% TFA as eluent) to give the title compound as a white solid (0.020 g, 0.045 mmol, 28%). $^1$H NMR (400 MHz, CDCl$_3$) δ 7.99 (t, J=0.5 Hz, 1H), 7.74 (s, 1H), 7.35-7.24 (m, 2H), 7.20-7.11 (m, 2H), 4.92 (s, 2H), 3.02-2.90 (m, 1H), 2.39 (s, 3H), δ 1.13 (d, J=7.2 Hz, 6H); MS: (ES) m/z calculated for C$_{19}$H$_{18}$ClF$_4$N$_5$O [M+H]$^+$ 444.1, found 443.9.

Example 5

Synthesis of 2-[4-chloro-5-methyl-3-(trifluoromethyl)pyrazol-1-yl]-N-[1-(4-fluorophenyl)-5-phenylpyrazol-4-yl]acetamide

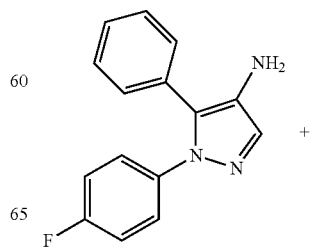

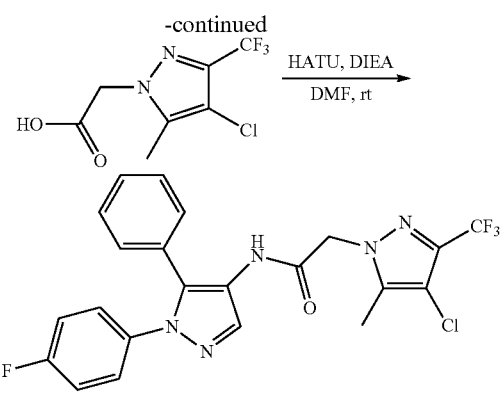

To a solution of 1-(4-fluorophenyl)-5-phenylpyrazol-4-amine (0.03 g, 0.12 mmol) in DMF (1.0 mL) was added 2-[4-chloro-5-methyl-3-(trifluoromethyl)pyrazol-1-yl]acetic acid (0.024 g, 0.12 mmol), followed by diisopropylethylamine (0.031 g, 0.24 mmol) and HATU (0.055 g, 0.14 mmol). After stirring at room temperature for 1 h, the reaction was diluted with water and the aqueous layer was extracted with ethyl acetate (2×5 mL). The combined organic layers were washed with brine, dried (Na$_2$SO$_4$), filtered, and concentrated in vacuo. The resulting crude product was purified by reverse phase HPLC (C18 column, acetonitrile-H$_2$O with 0.1% TFA as eluent) to give the title compound as a white solid (0.020 g, 0.045 mmol, 28%). $^1$H NMR (400 MHz, CDCl$_3$) δ 8.29 (s, 1H), 7.55 (s, 1H), 7.44-7.34 (m, 3H), 7.22-7.14 (m, 2H), 7.07-6.93 (m, 4H), 4.86 (s, 2H), 2.29 (s, 3H); MS: (ES) m/z calculated for C$_{22}$H$_{16}$ClF$_4$N$_5$O [M+H]$^+$ 478.1, found 477.8.

Example 6

Synthesis of N-[1-(4-fluorophenyl)-5-isopropylpyrazol-4-yl]-2-[2-methyl-4-(trifluoromethyl)imidazol-1-yl]butanamide

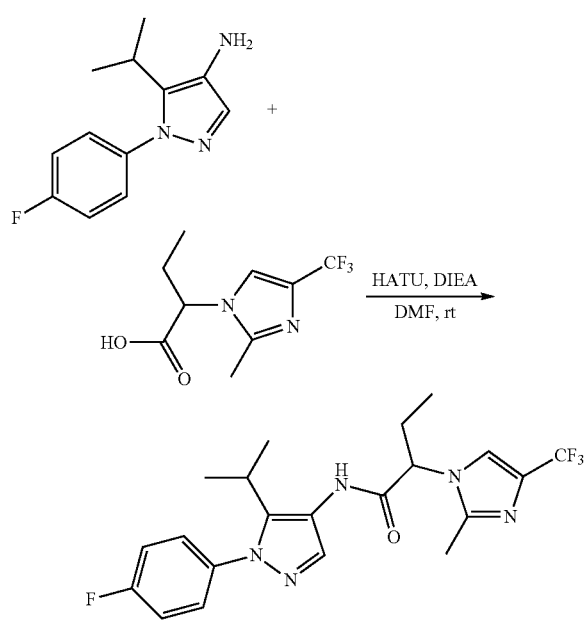

To a solution of 1-(4-fluorophenyl)-5-isopropylpyrazol-4-amine (0.03 g, 0.14 mmol) in DMF (1.0 mL) was added 2-[2-methyl-4-(trifluoromethyl)imidazol-1-yl]butanoic acid (0.032 g, 0.14 mmol), followed by diisopropylethylamine (0.042 g, 0.32 mmol) and HATU (0.057 g, 0.15 mmol). After stirring at room temperature for 1 h, the reaction was diluted with water and the aqueous layer was extracted with ethyl acetate (2×5 mL). The combined organic layers were washed with brine, dried (Na$_2$SO$_4$), filtered, and concentrated in vacuo. The resulting crude product was purified by reverse phase HPLC (C18 column, acetonitrile-H$_2$O with 0.1% TFA as eluent) to give the title compound as a white solid (0.015 g, 0.034 mmol, 25%). $^1$H NMR (400 MHz, CDCl$_3$) δ 7.85 (s, 1H), 7.47 (q, J=1.2 Hz, 1H), 7.34-7.24 (m, 2H), 7.21-7.11 (m, 2H), 6.98 (s, 1H), 4.65 (dd, J=10.1, 5.3 Hz, 1H), 3.00-2.88 (m, 1H), 2.49 (ddd, J=14.4, 7.4, 5.3 Hz, 1H), 2.45 (s, 3H), 2.13-2.00 (m, 1H), 1.11-0.97 (m, 9H); MS: (ES) m/z calculated for C$_{21}$H$_{23}$F$_4$N$_5$O [M+H]$^+$ 438.2, found 438.0.

Example 7

Synthesis of N-[1-(4-fluorophenyl)-5-isopropylpyrazol-4-yl]-2-[2-methyl-4-(trifluoromethyl)imidazol-1-yl]propanamide

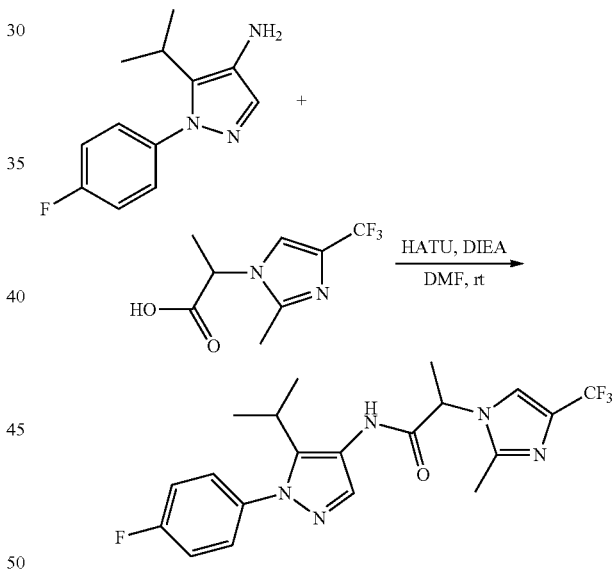

To a solution of 1-(4-fluorophenyl)-5-isopropylpyrazol-4-amine (0.03 g, 0.14 mmol) in DMF (1.0 mL) was added 2-[2-methyl-4-(trifluoromethyl)imidazol-1-yl]propanoic acid (0.031 g, 0.14 mmol), followed by diisopropylethylamine (0.042 g, 0.32 mmol) and HATU (0.057 g, 0.15 mmol). After stirring at room temperature for 1 h, the reaction was diluted with water and the aqueous layer was extracted with ethyl acetate (2×5 mL). The combined organic layers were washed with brine, dried (Na$_2$SO$_4$), filtered, and concentrated in vacuo. The resulting crude product was purified by reverse phase HPLC (C18 column, acetonitrile-H$_2$O with 0.1% TFA as eluent) to give the title compound as a white solid (0.0145 g, 0.034 mmol, 25%). $^1$H NMR (400 MHz, CDCl$_3$) δ 7.92 (d, J=0.6 Hz, 1H), 7.46 (q, J=1.2 Hz, 1H), 7.33-7.24 (m, 2H), 7.21-7.11 (m, 2H), 6.63 (s, 1H), 4.92 (q, J=7.3 Hz, 1H), 2.93 (m, 1H), 2.49 (s, 3H), 1.89 (d, J=7.3 Hz, 3H), 1.04 (dd, J=10.3, 7.2 Hz, 6H); MS: (ES) m/z calculated for $C_{20}H_{21}F_4N_5O$ [M+H]$^+$ 424.2, found 424.0.

Example 8

Synthesis of 2-[4-chloro-5-methyl-3-(trifluoromethyl)pyrazol-1-yl]-N-[1-(4-fluorophenyl)-5-isopropylpyrazol-4-yl]butanamide

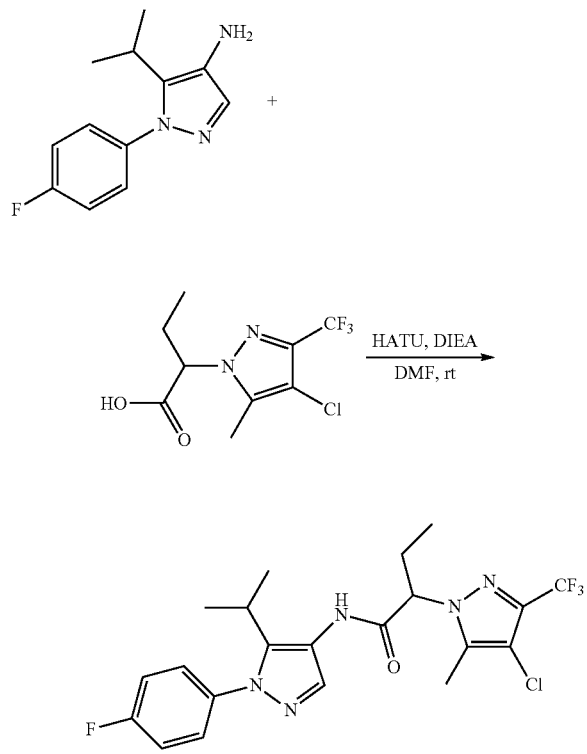

To a solution of 1-(4-fluorophenyl)-5-isopropylpyrazol-4-amine (0.03 g, 0.14 mmol) in DMF (1.0 mL) was added 2-[4-chloro-5-methyl-3-(trifluoromethyl)pyrazol-1-yl]butanoic acid (0.037 g, 0.14 mmol), followed by diisopropylethylamine (0.042 g, 0.32 mmol) and HATU (0.057 g, 0.15 mmol). After stirring at room temperature for 1 h, the reaction was diluted with water and the aqueous layer was extracted with ethyl acetate (2×5 mL). The combined organic layers were washed with brine, dried (Na$_2$SO$_4$), filtered, and concentrated in vacuo. The resulting crude product was purified by reverse phase HPLC (C18 column, acetonitrile-H$_2$O with 0.1% TFA as eluent) to give the title compound as a white solid (0.020 g, 0.042 mmol, 31%). $^1$H NMR (400 MHz, CDCl$_3$) δ 8.47 (s, 1H), 8.04 (s, 1H), 7.35-7.24 (m, 2H), 7.21-7.11 (m, 2H), 4.80 (dd, J=8.7, 6.5 Hz, 1H), 2.98 (m, 1H), 2.42-2.29 (m, 5H), 1.26 (d, J=7.2 Hz, 3H), 1.10 (d, J=7.1 Hz, 3H), 0.92 (t, J=7.3 Hz, 3H); MS: (ES) m/z calculated for $C_{21}H_{22}ClF_4N_5O$ [M+H]$^+$ 472.1, found 471.9.

Example 9

Synthesis of 2-[4-chloro-5-methyl-3-(trifluoromethyl)pyrazol-1-yl]-N-[1-(4-fluorophenyl)-5-isopropylpyrazol-4-yl]propanamide

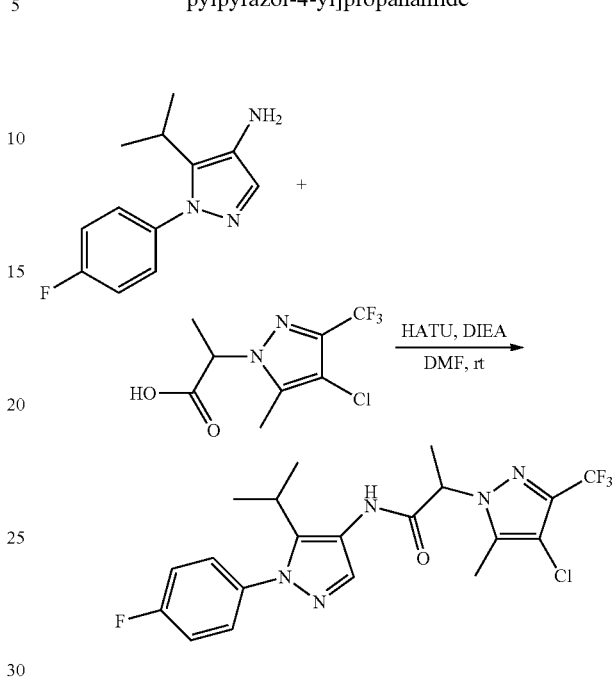

To a solution of 1-(4-fluorophenyl)-5-isopropylpyrazol-4-amine (0.03 g, 0.14 mmol) in DMF (1.0 mL) was added 2-[4-chloro-5-methyl-3-(trifluoromethyl)pyrazol-1-yl]propanoic acid (0.035 g, 0.14 mmol), followed by diisopropylethylamine (0.042 g, 0.32 mmol) and HATU (0.057 g, 0.15 mmol). After stirring at room temperature for 1 h, the reaction was diluted with water and the aqueous layer was extracted with ethyl acetate (2×5 mL). The combined organic layers were washed with brine, dried (Na$_2$SO$_4$), filtered, and concentrated in vacuo. The resulting crude product was purified by reverse phase HPLC (C18 column, acetonitrile-H$_2$O with 0.1% TFA as eluent) to give the title compound as a white solid (0.020 g, 0.044 mmol, 32%). $^1$H NMR (400 MHz, CDCl$_3$) δ 8.18 (s, 1H), 8.02 (s, 1H), 7.34-7.24 (m, 2H), 7.21-7.11 (m, 2H), 5.05 (q, J=7.2 Hz, 1H), 3.03-2.91 (m, 1H), 2.38 (s, 3H), 1.90 (d, J=7.2 Hz, 3H), 1.25 (dd, J=13.9, 7.1 Hz, 3H), 1.08 (d, J=7.2 Hz, 3H); MS: (ES) m/z calculated for $C_{20}H_{20}ClF_4N_5O$ [M+H]$^+$ 458.1, found 457.9.

Example 10

Synthesis of N-[5-tert-butyl-1-(4-fluorophenyl)pyrazol-4-yl]-2-[2-methyl-4-(trifluoromethyl)imidazol-1-yl]propanamide

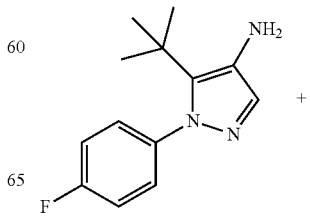

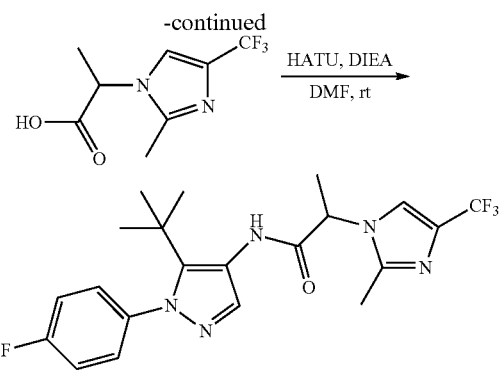

To a solution of 5-tert-butyl-1-(4-fluorophenyl)pyrazol-4-amine (0.03 g, 0.13 mmol) in DMF (1.0 mL) was added 2-[2-methyl-4-(trifluoromethyl)imidazol-1-yl]propanoic acid (0.029 g, 0.13 mmol), followed by diisopropylethylamine (0.033 g, 0.26 mmol) and HATU (0.054 g, 0.14 mmol). After stirring at room temperature for 1 h, the reaction was diluted with water and the aqueous layer was extracted with ethyl acetate (2×5 mL). The combined organic layers were washed with brine, dried ($Na_2SO_4$), filtered, and concentrated in vacuo. The resulting crude product was purified by reverse phase HPLC (C18 column, acetonitrile-$H_2O$ with 0.1% TFA as eluent) to give the title compound as a white solid (0.0145 g, 0.034 mmol, 25%). $^1$H NMR (400 MHz, $CDCl_3$) δ 7.77 (s, 1H), 7.45 (q, J=1.2 Hz, 1H), 7.33-7.24 (m, 2H), 7.16-7.07 (m, 2H), 6.89 (s, 1H), 4.90 (d, J=7.3 Hz, 1H), 2.47 (s, 3H), 1.86 (d, J=7.3 Hz, 3H), 1.11-1.03 (m, 9H); MS: (ES) m/z calculated for $C_{21}H_{23}F_4N_5O$ [M+H]$^+$ 438.2, found 438.0.

Example 11

Synthesis of N-[1-(4-chlorophenyl)-5-isopropylpyrazol-4-yl]-2-[5-methyl-3-(trifluoromethyl)-1,2,4-triazol-1-yl]propanamide

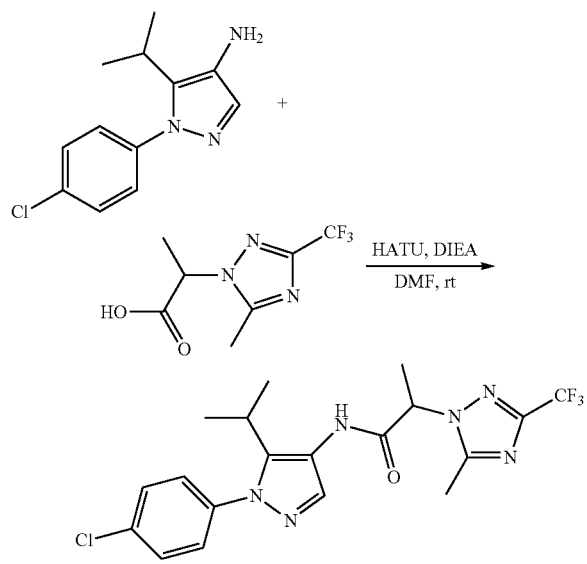

To a solution of 1-(4-chlorophenyl)-5-isopropylpyrazol-4-amine (0.054 g, 0.23 mmol) in DMF (1.0 mL) was added 2-[5-methyl-3-(trifluoromethyl)-1,2,4-triazol-1-yl]propanoic acid (0.051 g, 0.23 mmol), followed by diisopropylethylamine (0.059 g, 0.46 mmol) and HATU (0.105 g, 0.28 mmol). After stirring at room temperature for 1 h, the reaction was diluted with water and the aqueous layer was extracted with ethyl acetate (2×5 mL). The combined organic layers were washed with brine, dried ($Na_2SO_4$), filtered, and concentrated in vacuo. The resulting crude product was purified by reverse phase HPLC (C18 column, acetonitrile-$H_2O$ with 0.1% TFA as eluent) to give the title compound as a white solid (0.025 g, 0.057 mmol, 25%). $^1$H NMR (400 MHz, $CDCl_3$) δ 8.25 (s, 1H), 8.03 (d, J=0.6 Hz, 1H), 7.49-7.41 (m, 2H), 7.32-7.23 (m, 2H), 5.12 (q, J=7.2 Hz, 1H), 3.02 (m, 1H), 2.61 (s, 3H), 1.92 (d, J=7.2 Hz, 3H), 1.27 (d, J=7.2 Hz, 3H), 1.10 (d, J=7.2 Hz, 3H); MS: (ES) m/z calculated for $C_{19}H_{20}ClF_3N_6O$ [M+H]$^+$ 441.1, found 440.9.

Example 12

Synthesis of N-[1-(4-fluorophenyl)-5-isopropylpyrazol-4-yl]-2-[5-methyl-3-(trifluoromethyl)-1,2,4-triazol-1-yl]propanamide

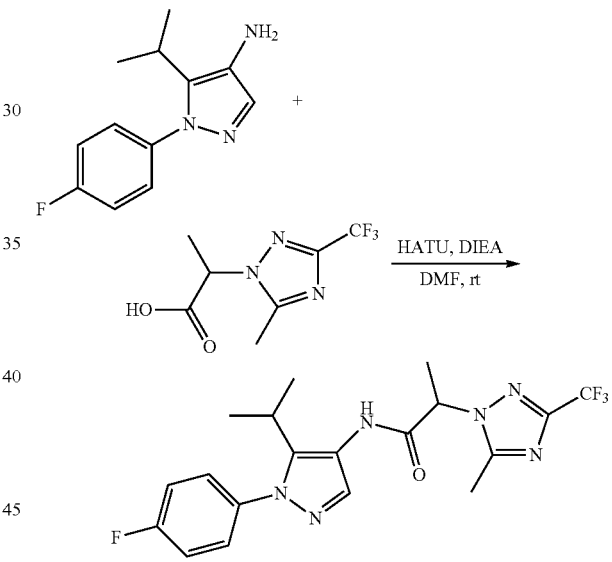

To a solution of 1-(4-fluorophenyl)-5-isopropylpyrazol-4-amine (0.050 g, 0.23 mmol) in DMF (1.0 mL) was added 2-[5-methyl-3-(trifluoromethyl)-1,2,4-triazol-1-yl]propanoic acid (0.051 g, 0.23 mmol), followed by diisopropylethylamine (0.059 g, 0.46 mmol) and HATU (0.105 g, 0.28 mmol). After stirring at room temperature for 1 h, the reaction was diluted with water and the aqueous layer was extracted with ethyl acetate (2×5 mL). The combined organic layers were washed with brine, dried ($Na_2SO_4$), filtered, and concentrated in vacuo. The resulting crude product was purified by reverse phase HPLC (C18 column, acetonitrile-$H_2O$ with 0.1% TFA as eluent) to give the title compound as a white solid (0.03 g, 0.0706 mmol, 31%). $^1$H NMR (400 MHz, $CDCl_3$) δ 8.24 (s, 1H), 8.04-7.99 (m, 1H), 7.35-7.25 (m, 2H), 7.22-7.11 (m, 2H), 5.13 (q, J=7.2 Hz, 1H), 3.05-2.93 (m, 1H), 2.62 (s, 3H), 1.93 (d, J=7.2 Hz, 3H), 1.27 (dd, J=7.2, 2.9 Hz, 3H), 1.10 (d, J=7.1 Hz, 3H); MS: (ES) m/z calculated for $C_{19}H_{20}F_4N_6O$ [M+H]$^+$ 425.2, found 425.0.

Example 13

Synthesis of 2-[4-chloro-5-methyl-3-(trifluoromethyl)pyrazol-1-yl]-N-[1-(4-fluorophenyl)-5-isopropylpyrazol-4-yl]-2-methyl-propanamide

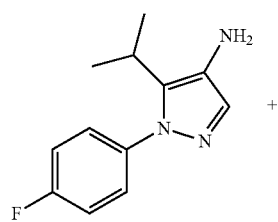

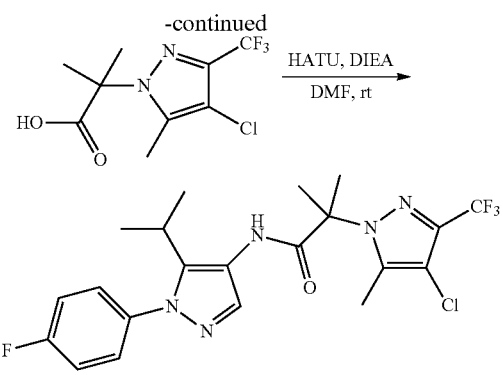

To a solution of 1-(4-fluorophenyl)-5-isopropylpyrazol-4-amine (0.03 g, 0.14 mmol) in DMF (1.0 mL) was added 2-[4-chloro-5-methyl-3-(trifluoromethyl)pyrazol-1-yl]-2-methyl-propanoic acid (0.037 g, 0.14 mmol), followed by diisopropylethylamine (0.042 g, 0.32 mmol) and HATU (0.057 g, 0.15 mmol). After stirring at room temperature for 1 h, the reaction was diluted with water and the aqueous layer was extracted with ethyl acetate (2×5 mL). The combined organic layers were washed with brine, dried (Na$_2$SO$_4$), filtered, and concentrated in vacuo. The resulting crude product was purified by reverse phase HPLC (C18 column, acetonitrile-H$_2$O with 0.1% TFA as eluent) to give the title compound as a white solid (0.025 g, 0.053 mmol, 39%). $^1$H NMR (400 MHz, CDCl$_3$) δ 7.91 (d, J=0.6 Hz, 1H), 7.33-7.25 (m, 2H), 7.20-7.10 (m, 2H), 6.61 (s, 1H), 2.92 (m, 1H), 2.37 (s, 3H), 1.97 (s, 6H), 1.03 (d, J=7.1 Hz, 6H); MS: (ES) m/z calculated for C$_{21}$H$_{22}$ClF$_4$N$_5$O [M+H]$^+$ 472.1, found 471.9.

Example 14

Synthesis of 2-[4-chloro-5-methyl-3-(trifluoromethyl)-1H-pyrazol-1-yl]-N-[1-(4-fluorophenyl)-5-methyl-1H-imidazol-4-yl]acetamide

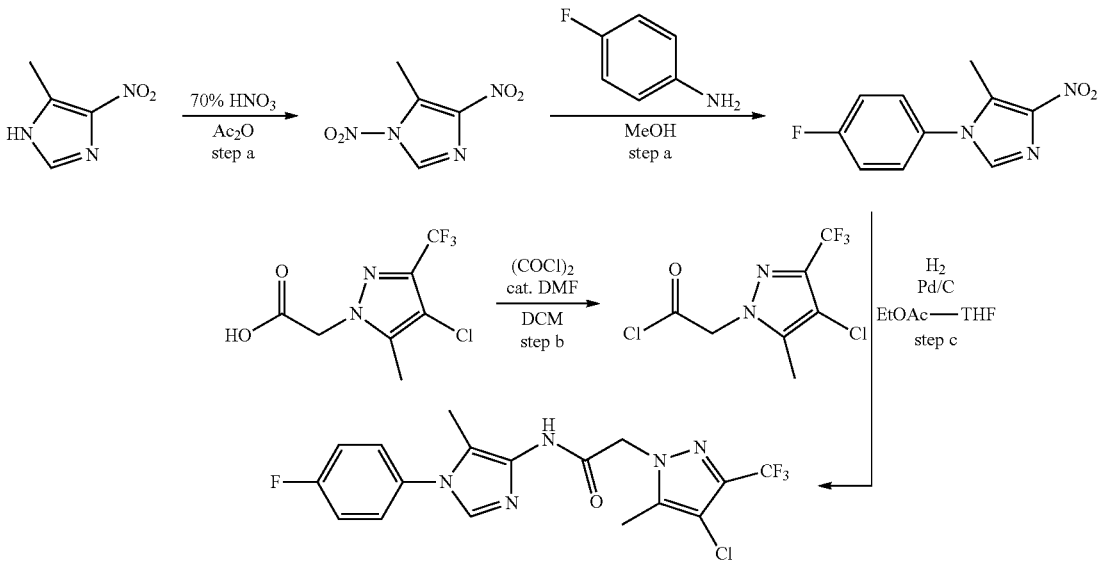

a) Acetic anhydride (1.65 mL) was added to 5-methyl-4-nitro-1H-imidazole (254 mg, 2.00 mmol) at room temperature. Nitric acid (70%, 200 µL) was added and the reaction was stirred for three days. The reaction was then poured onto ice. The product was extracted with dichloromethane three times. The combined organic layers was washed with saturated sodium bicarbonate solution and dried over anhydrous sodium sulfate. After removal of the solvent under reduced pressure, the crude 5-methyl-1,4-dinitro-1H-imidazole (235 mg) was dissolved in methanol (3 mL) at ambient temperature. A methanol (0.8 mL) solution of 4-fluoroaniline (157 µL, 1.63 mmol) was added dropwise and the reaction was stirred at this temperature for five days. Water was added to the reaction mixture and the product was extracted with dichloromethane three times. The combined organic layers were dried over anhydrous sodium sulfate. After removal of solvent under reduced pressure, the crude material was purified using silica gel column chromatography (33-60% ethyl acetate in hexanes) to give 5-methyl-4-nitro-1-(4-fluorophenyl)-1H-imidazole (157 mg, 0.712 mmol, 36% yield over two steps).

b) To a dichloromethane (2 mL) suspension of 4-chloro-5-methyl-3-trifluoromethyl-1H-pyrazole-1-acetic acid (186 mg, 0.768 mmol), was added oxalyl chloride (134 µL, 1.54 mmol) at ambient temperature. A catalytic amount of dimethylformamide (1.5 µL) was added and the reaction was stirred for two hours. Removal of solvent under reduced pressure gave the crude 4-chloro-5-methyl-3-trifluoromethyl-1H-pyrazole-1-acetyl chloride which was used without any further purification in the next step.

c) Both 5-methyl-4-nitro-1-(4-fluorophenyl)-1H-imidazole (77.8 mg, 0.352 mmol) and 4-chloro-5-methyl-3-trifluoromethyl-1H-pyrazole-1-acetyl chloride (crude, approximately 0.768 mmol) were dissolved in a mixture of ethyl acetate (5 mL) and tetrahydrofuran (5 mL). After flushing the reaction mixture with nitrogen, palladium on carbon (10%, wet, 23.3 mg) was added. The reaction mixture was hydrogenated using a Parr Apparatus for one and half hours at 40 psi. The reaction mixture was then filtered to remove palladium on carbon and after removal of the solvents under reduced pressure, the crude material was purified using silica gel column chromatography (1.3-2.6% methanol in ethyl acetate with 0.05% aqueous ammonia) to afford 2-[4-chloro-5-methyl-3-(trifluoromethyl)-1H-pyrazol-1-yl]-N-[1-(4-fluorophenyl)-5-methyl-1H-imidazol-4-yl]acetamide (13.6 mg, 0.0327 mmol, 9% yield). $^1$H NMR (400 MHz, CDCl$_3$) δ 7.73 (br, 1H), 7.39 (s, 1H), 7.24-7.29 (m, 2H), 7.19 (dd, J=8.4, 8.4 Hz, 1H), 4.94 (s, 2H), 2.35 (s, 3H), 2.04 (s, 3H); MS: (ES) m/z calculated for C$_{17}$H$_{14}$N$_5$OClF$_4$ [M+H]$^+$ 416.1, found 416.1.

Example 15

N-[1-(4-Chlorophenyl)-5-isopropyl-pyrazol-4-yl]-3-methyl-1-(trifluoromethyl)-5,6,7,8-tetrahydroimidazo[1,5-a]pyridine-5-carboxamide

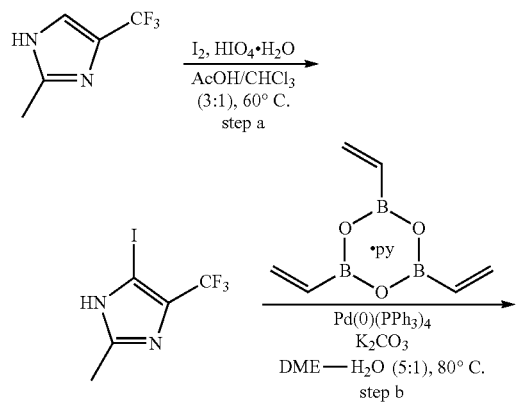

-continued

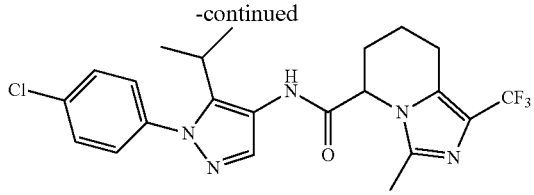

a) To 2-methyl-4-(trifluoromethyl)-1H-imidazole (1 g, 6.7 mmol) was added CHCl₃ (4.5 mL) and AcOH (13.5 mL) followed by I₂ (1.78 g, 6.99 mmol) and HIO₄·2H₂O (1.52 g, 6.7 mmol), and the resulting reaction mixture was stirred at 60° C. for 3 h. The reaction mixture was then poured into ice cold 10% aqueous sodium bisulphite solution (100 mL) and the aqueous layer was extracted with EtOAc (3×100 mL). The combined organic layers were washed with brine (100 mL), dried (MgSO₄) and concentrated in vacuo to obtain 5-iodo-2-methyl-4-(trifluoromethyl)-1H-imidazole (1.98 g) which was used as such in next step without further purification.

b) To a solution of 5-iodo-2-methyl-4-(trifluoromethyl)-1H-imidazole (1.98 g, 7.2 mmol) in DME (20 mL) and H₂O (4 mL) was added K₂CO₃ (10 g, 71.9 mmol), trivinylboronic anhydride pyridine complex (1.73 g, 7.19 mmol) and Pd(PPh₃)₄ (830 mg, 0.719 mmol). The resulting reaction mixture was stirred at 80° C. for 3 h. MeOH (100 mL) was then added to the reaction mixture and the mixture was filtered, concentrated in vacuo, and purified by flash chromatography (SiO₂, 10% MeOH/CH₂Cl₂) to obtain 2-methyl-4-(trifluoromethyl)-5-vinyl-1H-imidazole (911 mg, 5.17 mmol, 72% yield) as a brown syrup.

c) To a solution of 2-methyl-4-(trifluoromethyl)-5-vinyl-1H-imidazole (911 mg, 5.17 mmol) was added DMF (7 mL) and THF (3 mL), followed by K₂CO₃ (1.43 g, 10.35 mmol) and ethyl bromo acetate (687 µL, 6.2 mmol). The resulting mixture was then stirred overnight at room temperature. Water (50 mL) was added and the mixture was extracted with EtOAc (3×100 mL). The combined EtOAc layers were dried (MgSO₄), concentrated in vacuo, and purified by flash chromatography (SiO₂, 60% EtOAc/hexanes) to obtain the desired ethyl 2-[2-methyl-4-(trifluoromethyl)-5-vinyl-imidazol-1-yl]acetate (796 mg, 3.03 mmol, 59% yield) as a yellow oil.

d) To a cooled (−78° C.) solution of ethyl 2-[2-methyl-4-(trifluoromethyl)-5-vinyl-imidazol-1-yl]acetate (790 mg, 3.01 mmol) in THF (6 mL) under nitrogen atmosphere was added LDA (2 M, 3 mL, 6.03 mmol) drop wise. After stirring the reaction mixture at −78° C. for 15 min, allyl bromide (521 µL, 6.03 mmol) was added slowly and the reaction mixture was allowed to warm to room temperature and stirred for 2 h. A saturated NH₄Cl solution (20 mL) was added to the reaction mixture at 0° C. and the mixture was then extracted with EtOAc (2×100 mL). The combined EtOAc layers were then washed with brine (50 mL), dried (MgSO₄), concentrated in vacuo, and purified by flash chromatography (SiO₂, 80% EtOAc/hexanes) to obtain ethyl 2-[2-methyl-4-(trifluoromethyl)-5-vinyl-imidazol-1-yl]pent-4-enoate (127 mg, 0.42 mmol, 14% yield).

e) To ethyl 2-[2-methyl-4-(trifluoromethyl)-5-vinyl-imidazol-1-yl]pent-4-enoate (127 mg, 0.42 mmol) was added EtOH (2 mL) and 5 N NaOH (0.5 mL), and the resulting solution was stirred at room temperature for 1 h. 12 N HCl was added slowly at room temperature until the solution reached pH 2, followed by concentration in vacuo to obtain 2-[2-methyl-4-(trifluoromethyl)-5-vinyl-imidazol-1-yl]pent-4-enoic acid (100 mg, crude) which was used as such in the next step without further purification.

f) To 2-[2-methyl-4-(trifluoromethyl)-5-vinylimidazol-1-yl]pent-4-enoic acid (120 mg, 0.42 mmol) was added DMF (3 mL), Et₃N (500 µL, excess), 1-(4-chlorophenyl)-5-isopropylpyrazol-4-amine (100 mg, 0.42 mmol), and HATU (250 mg, excess) and the resulting mixture was stirred at room temperature for 1 h. Water (20 mL) was added and the mixture was extracted with EtOAc (2×50 mL). The combined organics were then dried (MgSO₄), concentrated in vacuo, and purified by flash chromatography (SiO₂, 80% EtOAc/hexanes) to obtain N-[1-(4-chlorophenyl)-5-isopropylpyrazol-4-yl]-2-[2-methyl-4-(trifluoromethyl)-5-vinylimidazol-1-yl]pent-4-enamide (147 mg, 0.3 mmol, 70% yield).

g) To N-[1-(4-chlorophenyl)-5-isopropylpyrazol-4-yl]-2-[2-methyl-4-(trifluoromethyl)-5-vinyl-imidazol-1-yl]pent-4-enamide (147 mg, 0.298 mmol) was added CH₂Cl₂ (10 mL) and benzylidene-bis(tricyclohexylphosphine)dichlororuthenium (Grubb's first generation catalyst, 122.6 mg, 0.149 mmol), and the resulting mixture was stirred at 45° C. for 3 h. The reaction mixture was then directly adsorbed on SiO₂ and purified by flash chromatography (SiO₂, 80% EtOAc/hexanes) to furnish N-[1-(4-chlorophenyl)-5-isopropylpyrazol-4-yl]-3-methyl-1-(trifluoromethyl)-5,6-dihydroimidazo[1,5-a]pyridine-5-carboxamide (30 mg, 0.064 mmol, 22% yield).

h) To N-[1-(4-chlorophenyl)-5-isopropylpyrazol-4-yl]-3-methyl-1-(trifluoromethyl)-5,6-dihydroimidazo[1,5-a]pyridine-5-carboxamide (30 mg, 0.064 mmol) was added EtOH (10 mL), 12 N HCl (4 drops), and PtO₂ (30 mg). The resulting suspension was evacuated with hydrogen gas twice and stirred under hydrogen gas (55 psi) on Parr shaker for 25 min. the reaction mixture was then filtered through a syringe filter, concentrated in vacuo, and purified by reverse phase HPLC (C18 column, acetonitrile-H₂O with 0.1% TFA as eluent) to give N-[1-(4-chlorophenyl)-5-isopropyl-pyrazol-4-yl]-3-methyl-1-(trifluoromethyl)-5,6,7,8-tetrahydroimidazo[1,5-a]pyridine-5-carboxamide (10 mg, 0.0172 mmol, 27% yield) as a TFA salt. ¹H NMR (400 MHz, Methanol-d₄) δ 7.62 (s, 1H), 7.57 (d, J=11.76 Hz, 2H), 7.42 (d, J=11.76 Hz, 2H), 5.20-5.22 (m, 1H), 3.0-3.18 (m, 2H), 2.8-2.95 (m, 1H), 2.40 (s, 3H), 2.32-2.55 (m, 2H), 1.80-2.05 (m, 2H), 1.27 (d, J=23.4 Hz, 3H), 1.24 (d, J=23.4 Hz, 3H); MS: (ES) m/z calculated for C₂₂H₂₃ClF₃N₅O [M+H]+ 466.9, found 466.1.

Example 15

Synthesis of 2-(4-chloro-5-methyl-3-(trifluoromethyl)-1H-pyrazol-1-yl)-N-(1-(4-fluorophenyl)-5-isopropyl-1H-pyrazol-4-yl)-6-hydroxyhexanamide

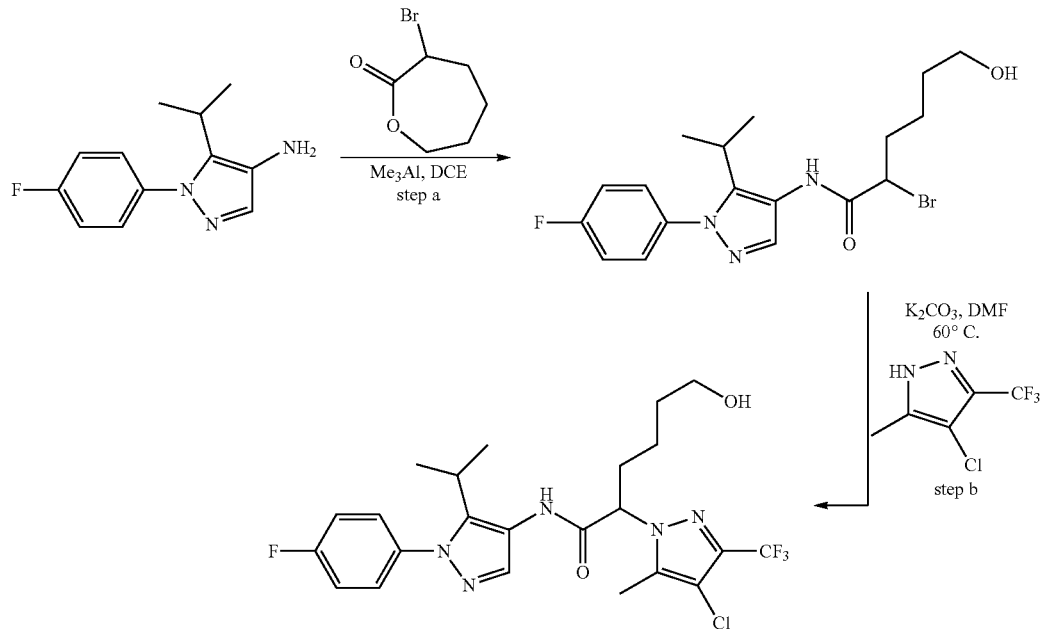 [SMILES: CC(C)c1c(N)cnn1-c1ccc(F)cc1 ; O=C1OCCCCC1Br ; CC(C)c1c(NC(=O)C(Br)CCCCO)cnn1-c1ccc(F)cc1 ; Cc1c(Cl)c(C(F)(F)F)nn1C(CCCCO)C(=O)Nc1cnn(-c2ccc(F)cc2)c1C(C)C ; Cc1[nH]nc(C(F)(F)F)c1Cl]

a) Trimethylaluminum (1.5 mL, 3 mmol, 2 M solution in toluene) was added portionwise to a solution of 1-(4-fluorophenyl)-5-isopropyl-1H-pyrazol-4-amine (329 mg, 1.5 mmol) and α-bromocaprolactone (319 mg, 1.65 mmol) in anhydrous dichloroethane (7.5 mL) under nitrogen at room temperature. After stirring for 1 h, the reaction was diluted with saturated NH$_4$Cl and the mixture was further diluted with 20 mL of EtOAc and 1.5 mL of 6 N HCl. The organic layer was washed with water and brine, dried over MgSO$_4$, filtered, and concentrated in vacuo. The crude material was used without further purification.

b) The residue from step a (310 mg, 0.75 mmol) and 4-chloro-5-methyl-3-(trifluoromethyl)-1H-pyrazole (277 mg, 1.5 mmol) was dissolved in DMF (1.5 mL) and treated with K$_2$CO$_3$ (311 mg, 2.25 mmol). After stirring at 60° C. for 2.5 h, the reaction mixture was diluted with EtOAc (20 mL) and washed with water and brine. The organic layer was dried on MgSO$_4$, filtered, and concentrated in vacuo to give a residue that was purified by flash chromatography (SiO$_2$, 35-100% EtOAc/hexanes) to give the titled compound (300 mg, 0.58 mmol, 78%) as a colorless oil that solidified on cooling. $^1$H NMR (400 MHz, CDCl$_3$) δ 8.37 (s, 1H), 8.03 (s, 1H), 7.32-7.27 (m, 2H), 7.18-7.13 (m, 2H), 4.89 (dd, J=9.4, 6.2 Hz, 1H), 3.65 (ddd, J=12.6, 10.6, 6.7 Hz, 2H), 3.00-2.93 (m, 1H), 2.37 (s, 3H), 1.65-1.56 (m, 4H), 1.48-1.37 (m, 1H), 1.32-1.28 (m, 1H), 1.25 (d, J=7.0 Hz, 3H), 1.08 (d, J=7.0 Hz, 3H); MS: (ES) m/z calculated for C$_{23}$H$_{27}$ClF$_4$N$_5$O$_2$ [M+H]$^+$ 516.2, found 516.1.

Example 15

Synthesis of (S)—N-(1-(4-chlorophenyl)-5-isopropyl-1H-pyrazol-4-yl)-2-(2-methyl-4-(trifluoromethyl)-1H-imidazol-1-yl)propanamide

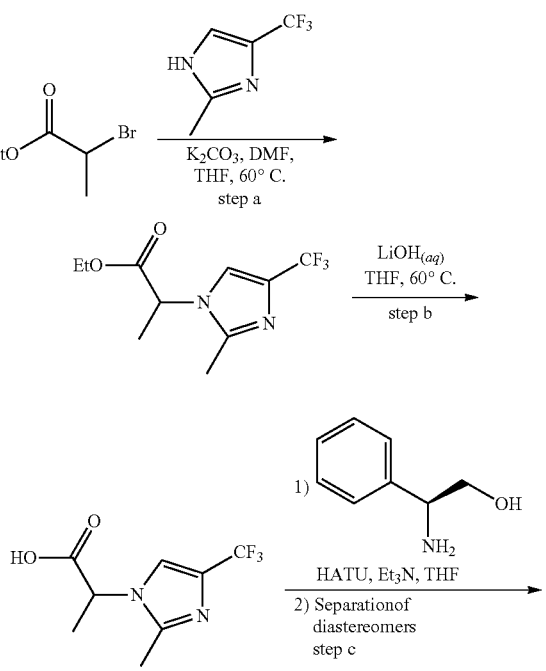

-continued

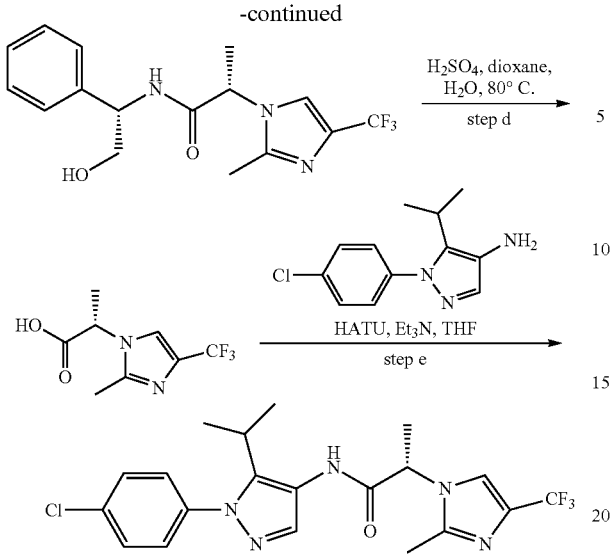

a) A solution of ethyl 2-bromopropionate (3.98 g, 22 mmol), 4-chloro-5-methyl-3-(trifluoromethyl)-1H-pyrazole (3.00 g, 20 mmol), and $K_2CO_3$ (5.53 g, 40 mmol) in THF/DMF (2:1, 39 mL) was allowed to stir at 45° C. for 16 h. The mixture was then concentrated in vacuo and diluted with EtOAc (70 mL). The organic layer was washed with water and brine, dried over $MgSO_4$, filtered, and concentrated in vacuo to give the product (5.3 g) as a colorless oil that was used without further purification.

b) The crude material from step a was dissolved in THF (40 mL) and treated with 2 M LiOH (15 mL, 30 mmol). The slurry was heated to 60° C. for 1 h and then concentrated. The residue was diluted with water (20 mL) and adjusted to pH 2 with $H_2SO_4$ and NaOH, providing the desired acid as a colorless solid (3.03 g, 13.6 mmol, 68% over two steps).

c) The acid intermediate (1.00 g, 4.5 mmol) from step b and (S)-phenylglycinol (679 mg, 4.95 mmol) were slurried in THF (22 mL) and $Et_3N$ (1.25 mL, 9 mmol). HATU (1.88 g, 4.95 mmol) was added and the slurry was stirred for 4 h. The volatiles were removed in vacuo and the residue diluted in EtOAc. The organic layer was washed with 3 M KOH (2×10 mL) and brine and was then loaded onto silica gel. The crude material was purified by flash chromatography ($SiO_2$, 3-4% methanol/$CH_2Cl_2$) to give two diastereomeric products as colorless solids. The first eluting isomer (500 mg) was obtained in >99:1 diastereomeric ratio (by $^1$H NMR).

d) The first eluting product from step c (484 mg, 1.4 mmol) was dissolved in dioxane (5.6 mL) and treated with 6 M $H_2SO_4$ (3.5 mL, 21 mmol). The slurry was heated at 80° C. for 6 h and then cooled. The crude residue was then purified by reverse phase HPLC (C18 column, acetonitrile-$H_2O$ with 0.1% TFA as eluent). The resulting lactone. TFA salt was neutralized and salted with HCl and dried to provide the enantiomerically enriched acid as a colorless solid (301 mg, 1.16 mmol, 83%).

e) To a solution of the acid intermediate from step d (23.6 mg, 0.1 mmol) and 1-(4-chlorophenyl)-5-isopropyl-1H-pyrazol-4-amine (16.6 mg, 0.064 mmol) in DMF (0.5 mL) was added $Et_3N$ (20 µL, 0.13 mmol) and HATU (31.6 mg, 0.083 mmol). After stirring 35 min, the slurry was concentrated under reduced pressure and the residue was purified by reverse phase HPLC (C18 column, acetonitrile-$H_2O$ with 0.1% TFA as eluent). The residue was neutralized and salted with HCL to provide the titled compound hydrochloride salt as a colorless solid (12.3 mg). $^1$H NMR (400 MHz, $CD_3OD$) δ 8.28 (d, J=1.6 Hz, 1H), 7.63 (s, 1H), 7.57 (ddd, J=9.7, 5.1, 3.1 Hz, 2H), 7.41 (ddd, J=9.7, 5.0, 3.1 Hz, 2H), 5.38 (q, J=7.0 Hz, 1H), 3.03 (hept, J=7.0 Hz, 1H), 2.65 (s, 3H), 1.91 (d, J=7.0 Hz, 3H), 1.23 (d, J=7.1 Hz, 3H), 1.22 (d, J=7.0 Hz, 3H); MS: (ES) m/z calculated for $C_{20}H_{22}ClF_3N_5O$ [M+H]$^+$ 440.1, found 439.9. Retention time on chiral HPLC: 5.9 min (RegisPack cat#783104, 25 cm×4.6 mm, 5 micron; eluent: 0.1% diethylamine/IPA, 1.0 ml/min). The er is determined to be 20:1 with the (R)-enantiomer having a retentime of 3.4 min. Absolute configuration of the (R)-enantiomer was confirmed by an independent synthesis from methyl (L)-lactate.

Example 16

Synthesis of (S)—N-(1-(4-fluorophenyl)-5-isopropyl-1H-pyrazol-4-yl)-2-(2-methyl-4-(trifluoromethyl)-1H-imidazol-1-yl)propanamide trifluoroacetic acid salt

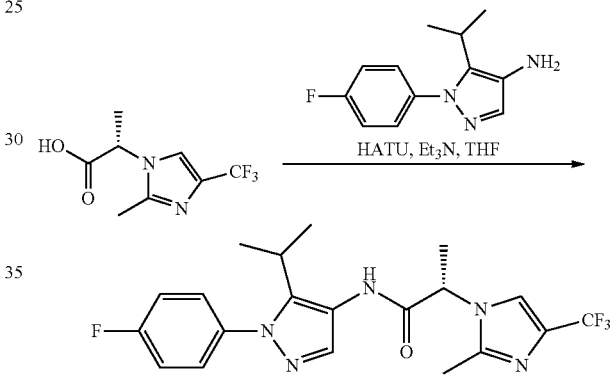

The titled compound was prepared using the procedure as described in Example 15, substituting 1-(4-chlorophenyl)-5-isopropyl-1H-pyrazol-4-amine for 1-(4-fluorophenyl)-5-isopropyl-1H-pyrazol-4-amine in step e. The product was isolated as the TFA salt $^1$H NMR (400 MHz, $CD_3OD$) δ 7.85 (d, J=1.2 Hz, 1H), 7.59 (d, J=1.2 Hz, 1H), 7.47-7.41 (m, 2H), 7.32-7.26 (m, 2H), 5.21 (q, J=7.0 Hz, 1H), 2.99 (hept, J=7.0 Hz, 1H), 2.50 (s, 3H), 1.83 (d, J=7.1 Hz, 3H), 1.19 (d, J=6.6 Hz, 3H), 1.18 (d, J=6.7 Hz, 3H); MS: (ES) m/z calculated for $C_{20}H_{22}F_4N_5O$ [M+H]$^+$ 424.2, found 423.9. Retention time on chiral HPLC: 13.1 min (RegisPack cat#783104, 25 cm×4.6 mm, 5 micron; eluent: 0.1% diethylamine/IPA, 0.4 ml/min). The er is determined to be 40:1 with the (R)-enantiomer having a retention time of 8.2 min.

Example 17

Synthesis of N-[5-ethoxy-1-(4-fluorophenyl)pyrazol-4-yl]-2-[2-methyl-4-(trifluoromethyl)imidazol-1-yl]propanamide

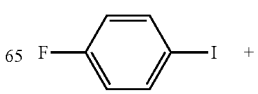

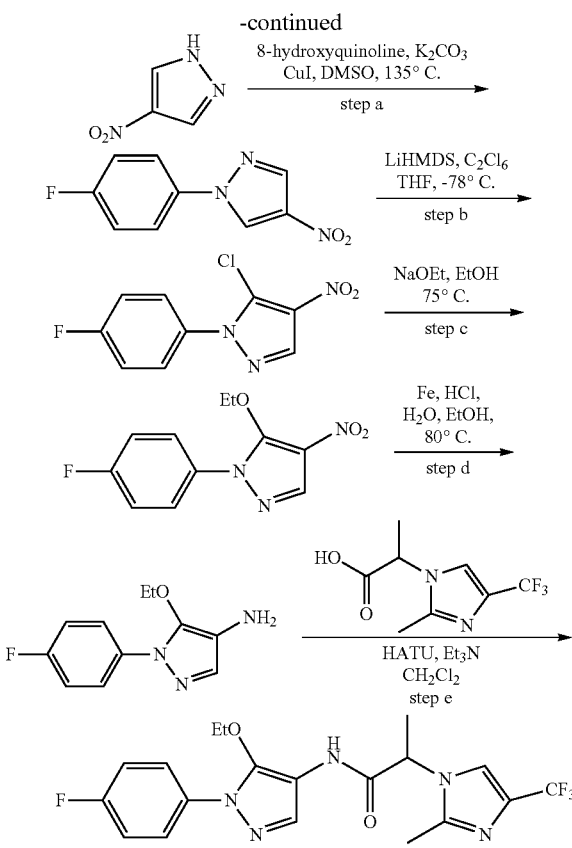

a) A mixture of 4-iodofluorobenzene (2.42 g, 11 mmol), 4-nitro-1H-pyrazole (1.00 g, 10 mmol), 8-hyroxyquinoline (0.15 g, 1 mmol), CuI (0.192 g, 1 mmol), and potassium carbonate (2.78 g, 20 mmol) in DMSO (20 mL) was heated at 135° C. overnight. After cooling to room temperature, the reaction mixture was diluted with 30 mL of water and extracted with ethyl acetate. The organic layer was washed with aqueous saturated sodium bicarbonate, dried ($Na_2SO_4$), filtered, and concentrated in vacuo. Purification by flash chromatography ($SiO_2$, 10%-20% EtOAc in hexanes) gave 1.02 g (4.9 mmol, 49%) of the desired product.

b) To a stirred solution of 1-(4-fluorophenyl)-4-nitropyrazole (1.02 g, 4.9 mmol) in 10 mL of THF was added LiHMDS (1 M in THF, 5.8 mL, 5.8 mmol) slowly at −78° C. under nitrogen. After stirring 30 minutes, 1,1,1,2,2,2-hexachloroethane (1.31 g, 5.5 mmol) in 6 mL of THF was added dropwise. The reaction mixture was stirred for 1 h followed by quenching with 20 ml, of aqueous saturated $NH_4Cl$. The reaction mixture was then warmed to room temperature and extracted with EtOAc. The organic layer was dried ($Na_2SO_4$), filtered, and concentrated in vacuo. Purification by flash chromatography ($SiO_2$, 5%-15% EtOAc in hexanes) provided 0.613 g of the desired product (2.5 mmol, 52%).

c) A mixture of 5-chloro-1-(4-fluorophenyl)-4-nitropyrazole (0.121 g, 0.5 mmol) and sodium ethoxide (0.137 g, 2 mmol) in 2 mL of EtOH was heated at 75° C. overnight. After cooling to room temperature, the reaction mixture was diluted with 20 mL of aqueous saturated sodium bicarbonate and extracted with EtOAc. The organic layer was washed with brine, dried ($Na_2SO_4$), filtered, and concentrated in vacuo. The crude material was used directly in the next step.

d) A mixture of the crude product from step c, iron (0.114 g, 2 mmol), and 100 μL of aqueous 6 N HCl in 2 mL of EtOH was heated at 80° C. for 20 minutes. After cooling to room temperature, the reaction mixture was diluted with 20 mL of aqueous saturated sodium bicarbonate and 40 mL of EtOAc. The resulting suspension was stirred for 10 minutes then filtered through a pad of Celite. The organic layer was separated, washed with brine, dried ($Na_2SO_4$), filtered, and concentrated in vacuo. The crude material was used directly in the next step.

e) A mixture of the crude product from step d, 2-[2-methyl-4-(trifluoromethyl)imidazol-1-yl]propanoic acid (0.112 g, 0.5 mmol), HATU (0.191 g, 0.5 mmol), and 100 μL of $Et_3N$ in 1 mL of $CH_2Cl_2$ was stirred at room temperature. After 30 minutes, the reaction mixture was diluted with 10 mL of aqueous saturated sodium bicarbonate and extracted with EtOAc. The organic layer was washed with brine, dried ($Na_2SO_4$), filtered, and concentrated in vacuo. Purification by reverse phase HPLC (C18 column, acetonitrile-$H_2O$ with 0.1% TFA as eluent) followed by flash chromatography ($SiO_2$, 60%-100% EtOAc in hexanes) afforded the title compound as a colorless solid (0.020 g, 0.047 mmol, 2.4% for 5 steps). $^1H$ NMR (400 MHz, $CDCl_3$) 7.85 (s, 1H), 7.67-7.55 (m, 2H), 7.44 (s, 1H), 7.31-7.08 (m, 2H), 6.82 (s, 1H), 4.88 (q, J=7.2 Hz, 1H), 3.84 (q, J=7.1 Hz, 2H), 2.45 (s, 3H), 1.85 (d, J=7.2 Hz, 3H), 1.65 (s, 3H), 1.17 (t, J=7.1 Hz, 3H). MS: (ES) m/z calculated for $C_{19}H_{19}F_4N_5O_2$ [M+H]$^+$ 426.2, found 426.1.

Example 18

Synthesis of N-[5-chloro-1-(4-fluorophenyl)pyrazol-4-yl]-2-[2-methyl-4-(trifluoromethyl)imidazol-1-yl]propanamide

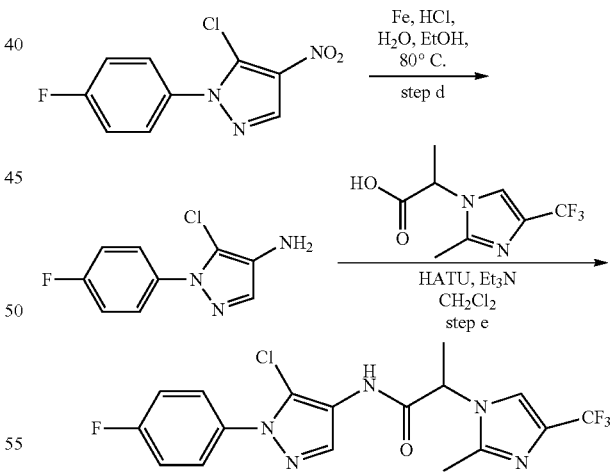

A sample of 5-chloro-1-(4-fluorophenyl)-4-nitropyrazole generated in the previous example was subsequently carried through steps d and e. The titled compound was isolated during the purification described in Example 17, providing 2.5 mg as a colorless solid. $^1H$ NMR (400 MHz, $CDCl_3$) δ 8.13 (s, 1H), 7.48-7.52 (m, 2H), 7.45 (s, 1H), 7.16-7.21 (m, 2H), 6.72 (s, 1H), 4.92 (q, J=7.2 Hz, 1H), 2.49 (s, 3H), 1.88 (d, J=7.2 Hz, 3H). MS: (ES) m/z calculated for $C_{17}H_{14}ClF_4N_5O$ [M+H]$^+$ 416.1, found 416.1.

Example 19

Synthesis of N-[5-isopropoxy-1-(4-fluorophenyl)pyrazol-4-yl]-2-[2-methyl-4-(trifluoromethyl)imidazol-1-yl]propanamide

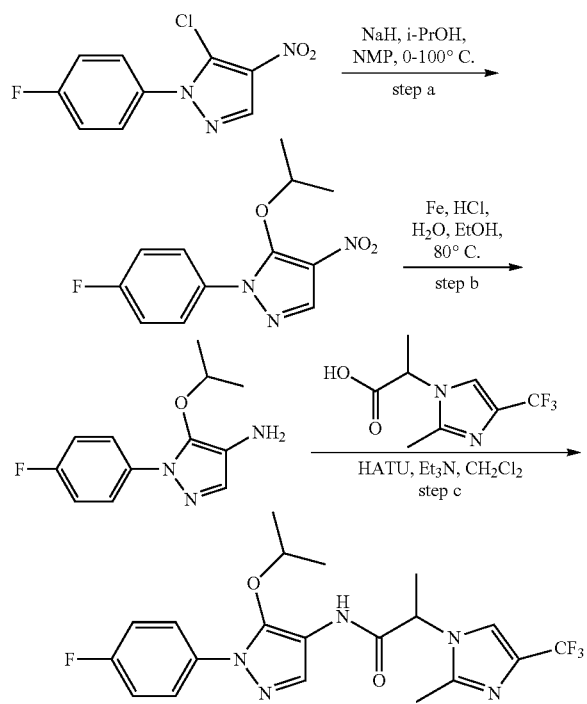

a) To a stirred solution of isopropanol (0.12 g, 2 mmol) in 1 mL of NMP was added NaH (0.085 g, 2 mmol) portionwise at 0° C. The reaction mixture was warmed to room temperature for 10 minutes before the addition of 5-chloro-1-(4-fluorophenyl)-4-nitropyrazole (0.24 g, 1 mmol) in one portion. The reaction slurry was then heated at 100° C. for 3 h. After cooling to room temperature, the reaction was quenched with aqueous saturated sodium bicarbonate and extracted with EtOAc. The organic layer was dried ($Na_2SO_4$), filtered, and concentrated in vacuo. The crude material was used directly in the next step.

b) A mixture of the crude product from step a, iron (0.23 g, 4 mmol), and 100 µL of aqueous 6 N HCl in 2 mL of EtOH was heated at 80° C. for 20 minutes. After cooling to room temperature, the reaction mixture was diluted with 20 mL of aqueous saturated sodium bicarbonate and 40 mL of EtOAc. The resulting suspension was stirred for 10 minutes then filtered through a pad of Celite. The organic layer was separated, washed with brine, dried ($Na_2SO_4$), filtered, and concentrated in vacuo. The crude material was used directly in the next step.

c) A mixture of crude 1-(4-fluorophenyl)-5-isopropoxy-pyrazol-4-amine (prepared in step b, 0.032 g, 0.13 mmol), 2-[2-methyl-4-(trifluoromethyl)imidazol-1-yl]propanoic acid (0.031 g, 0.13 mmol), HATU (0.057 g, 0.13 mmol), and 100 µL of $Et_3N$ in 1 mL of $CH_2Cl_2$ was stirred at room temperature. After 30 min, the reaction mixture was diluted with 10 mL of aqueous saturated sodium bicarbonate and extracted with EtOAc. The organic layer was washed with brine, dried ($Na_2SO_4$), filtered, and concentrated in vacuo. Purification by reverse phase HPLC (C18 column, acetonitrile-$H_2O$ with 0.1% TFA as eluent) provided the title compound as a colorless solid (0.030 g, 0.068 mmol, 52% for 3 steps). $^1$H NMR (400 MHz, $CD_3OD$) δ 7.81 (s, 1H), 7.70 (s, 1H), 7.68-7.57 (m, 2H), 7.30-7.19 (m, 2H), 5.16 (q, J=6.5 Hz, 1H), 4.26 (he, J=6.1 Hz, 1H), 2.47 (s, 3H), 1.80 (d, J=6.5 Hz, 3H), 1.14 (d, J=6.1, 6 H). MS: (ES) m/z calculated for $C_{20}H_{21}F_4N_5O_2$ [M+H]$^+$ 439.2, found 439.4.

Example 20

Synthesis of N-[5-(dimethylamino)-1-(4-fluorophenyl)pyrazol-4-yl]-2-[2-methyl-4-(trifluoromethyl)imidazol-1-yl]propanamide

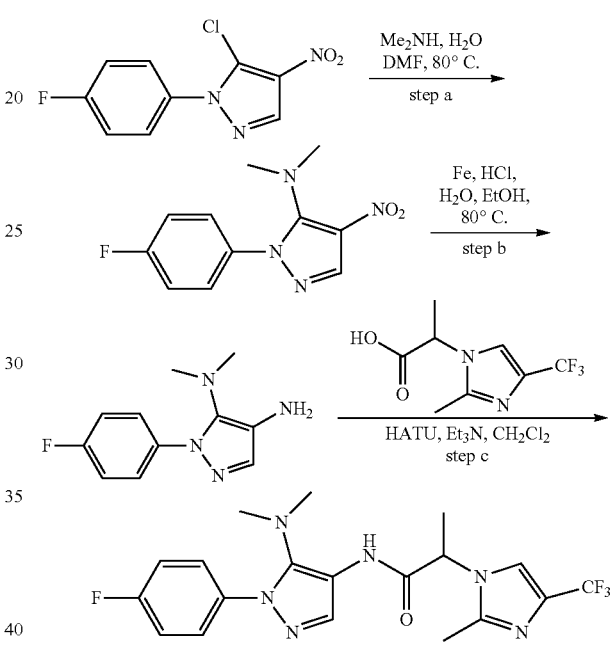

a) A mixture of 5-chloro-1-(4-fluorophenyl)-4-nitropyrazole (0.20 g, 0.8 mmol) and dimethylamine (2 M in water, 0.80 mL, 1.6 mmol) in 1 mL of DMF was heated at 80° C. After cooling to room temperature, the reaction was diluted with 20 mL of water and extracted with EtOAc. The organic layer was washed with brine, dried ($Na_2SO_4$), filtered, and concentrated in vacuo. The crude material was used directly in the next step.

b) A mixture of crude product from step a, iron (0.14 g, 2.5 mmol), and 100 µL of aqueous 6 N HCl in 1 mL of EtOH was heated at 80° C. for 20 minutes. Upon cooling to room temperature, the reaction mixture was diluted with 20 mL of aqueous saturated sodium bicarbonate, and 40 mL of EtOAc. The resulting suspension was stirred for 10 minutes and then filtered through celite. The organic layer was separated, washed with brine, dried ($Na_2SO_4$), filtered, and concentrated in vacuo. The crude material was used directly in the next step.

c) A mixture of crude 2-(4-fluorophenyl)-N3,N3-dimethyl-pyrazole-3,4-diamine (from step b, 0.042 g, 0.18 mmol), 2-[2-methyl-4-(trifluoromethyl)imidazol-1-yl]propanoic acid (0.060 g, 0.27 mmol), HATU (0.10 g, 0.27 mmol), and 100 µL of $Et_3N$ in 1 mL of $CH_2Cl_2$ was stirred at room temperature. After 30 minutes, the reaction mixture was diluted with 10 mL of aqueous saturated sodium bicarbonate and extracted with EtOAc. The organic layer was washed with brine, dried (Na$_2$SO$_4$), filtered, and concentrated in vacuo. Purification by reverse phase HPLC (C18 column, acetonitrile-H$_2$O with 0.1% TFA as eluent) afforded the title compound as a colorless solid (0.019 g, 0.045 mmol, 25% for 3 steps). $^1$H NMR (400 MHz, CDCl$_3$) δ 7.77 (s, 1H), 7.53-7.43 (m, 2H), 7.27 (s, 1H), 7.17-7.08 (m, 2H), 6.91 (s, 1H), 4.90 (q, J=7.2 Hz, 1H), 2.53 (s, 6H), 2.45 (s, 3H), 1.85 (d, J=7.2 Hz, 3H). MS: (ES) m/z calculated for C$_{19}$H$_{20}$F$_4$N$_6$O$_1$ [M+H]$^+$ 424.2, found 424.1.

Example 21

Synthesis of N-[1-(4-chlorophenyl)-5-isopropyltriazol-4-yl]-2-[2-methyl-4-(trifluoromethyl)imidazol-1-yl]propanamide

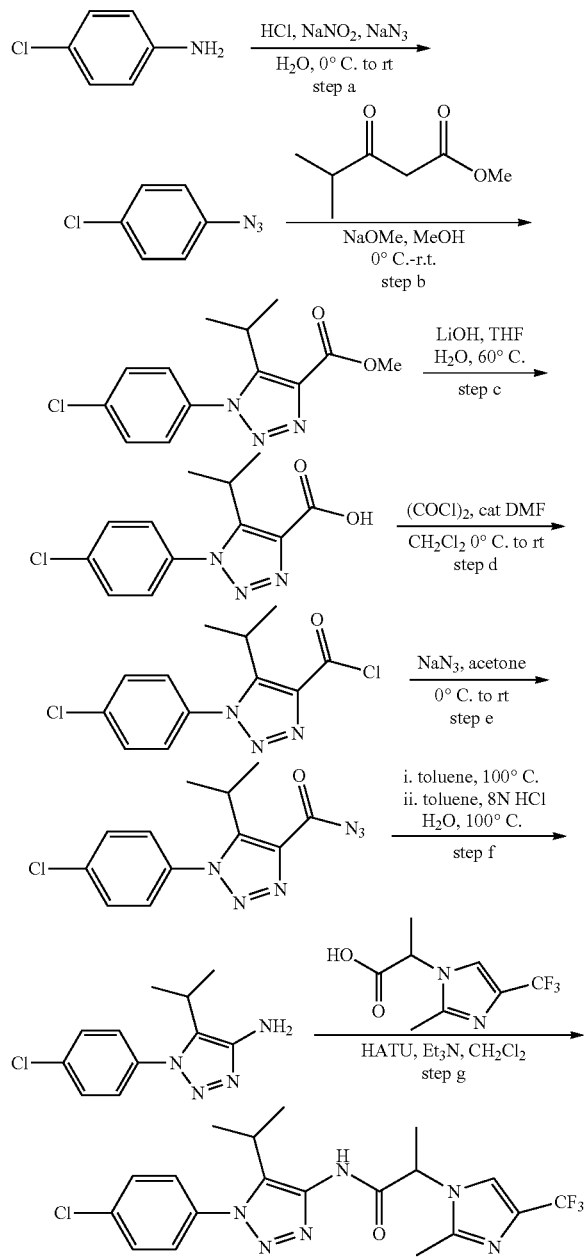

a) To a cooled (0° C.) slurry of 4-chloroaniline (0.25 g, 2 mmol) in 20 mL of aqueous 4 N HCl was added a solution of sodium nitrite (0.14 g, 2 mmol) in 200 μL of H$_2$O. After 10 minutes, sodium azide (0.16 g, 2.4 mmol) was added and the reaction mixture was stirred at room temperature. After 2 h, the reaction mixture was extracted with ethyl acetate. The organic layer was washed with aqueous saturated sodium bicarbonate, dried (Na$_2$SO$_4$), filtered, and concentrated in vacuo. The crude material was used directly in the next step.

b) To stirring solution of methyl 4-methyl-3-oxo-pentanoate (341 μL, 2.4 mmol) in 2 mL of MeOH was added NaOMe at 0° C. After 5 minutes, the residue from step a in 1 mL of MeOH was added in one portion. The reaction mixture was then allowed to stir at room temperature overnight. The mixture was then diluted with 20 mL of aqueous saturated sodium bicarbonate and extracted with EtOAc. The organic layer was washed with brine, dried (Na$_2$SO$_4$), filtered, and concentrated in vacuo. Purification by flash chromatography (SiO$_2$, 10%-20% EtOAc in hexanes) gave 0.11 g of the desired product (0.39 mmol, 20%).

c) A mixture of methyl 1-(4-chlorophenyl)-5-isopropyl-triazole-4-carboxylate (0.11 g, 0.39 mmol) and lithium hydroxide in 4 mL of THF and 1 mL of H$_2$O was heated at 60° C. After 2 h, the slurry was cooled to room temperature, adjusted to pH 5, and extracted with EtOAc. The organic layer was washed with brine, dried (Na$_2$SO$_4$), filtered, and concentrated in vacuo. The crude material was used directly in the next step.

d) To the product from step c in 1 mL of CH$_2$Cl$_2$ at 0° C. was added oxalyl chloride (67 μL, 0.78 mmol) and two drops of DMF. After 5 minutes, the reaction mixture was warmed to room temperature. After 2 h, the reaction slurry was concentrated in vacuo. The crude material was used directly in the next step.

e) The product from step d was diluted in 2 mL of acetone, cooled to 0° C., and treated with NaN$_3$ (1 g). The reaction slurry was warmed to room temperature for 10 minutes. The slurry was then diluted with 10 mL of aqueous saturated sodium bicarbonate and extracted with EtOAc. The organic layer was washed with brine, dried (Na$_2$SO$_4$), filtered, and concentrated in vacuo. The crude material was used directly in the next step.

f) A solution of the product from step e in 3 mL of toluene was heated at 100° C. for 2 h. To this solution was added aqueous 8 N HCl (200 μL, 1.6 mmol) at 100° C. and the mixture was stirred for another 10 minutes. After cooling to room temperature, the reaction mixture was diluted with 20 mL of aqueous saturated sodium bicarbonate and extracted with EtOAc. The organic layer was washed with brine, dried (Na$_2$SO$_4$), filtered, and concentrated in vacuo. Purification by flash chromatography (SiO$_2$, 10%-40% EtOAc in hexanes) gave 0.05 g of desired aniline product (0.21 mmol, 54%).

g) A mixture of 1-(4-chlorophenyl)-5-isopropyltriazol-4-amine (from step f, 0.025 g, 0.11 mmol), 2-[2-methyl-4-(trifluoromethyl)imidazol-1-yl]propanoic acid (0.031 g, 0.13 mmol), HATU (0.057 g, 0.13 mmol), and 100 μL of Et$_3$N in 1 mL of CH$_2$Cl$_2$ was stirred at room temperature. After 30 minutes, the reaction mixture was diluted with 10 mL of aqueous saturated sodium bicarbonate and extracted with EtOAc. The organic layer was washed with brine, dried (Na$_2$SO$_4$), filtered, and concentrated in vacuo. Purification by reverse phase HPLC (C18 column, acetonitrile-H$_2$O with 0.1% TFA as eluent) provided the title compound as a colorless solid (0.0051 g, 0.011 mmol, 10%). $^1$H NMR (400

MHz, CDCl$_3$) δ 9.14 (s, 1H), 7.65 (s, 1H), 7.54 (d, J=8.3 Hz, 2H), 7.34 (d, J=8.3 Hz, 2H), 5.26 (q, J=7.4 Hz, 1H), 3.0-2.98 (m, 1H), 2.62 (s, 3H), 1.86 (d, J=7.4 Hz, 3H), 1.14 (t, J=6.4 Hz, 6H). MS: (ES) m/z calculated for C$_{19}$H$_{20}$ClF$_3$N$_6$O [M+H]$^+$ 441.1, found 441.2.

Example 22

Synthesis of 2-[4-chloro-5-methyl-3-(trifluoromethyl)pyrazol-1-yl]-N-[1-(4-fluorophenyl)pyrazol-4-yl]acetamide

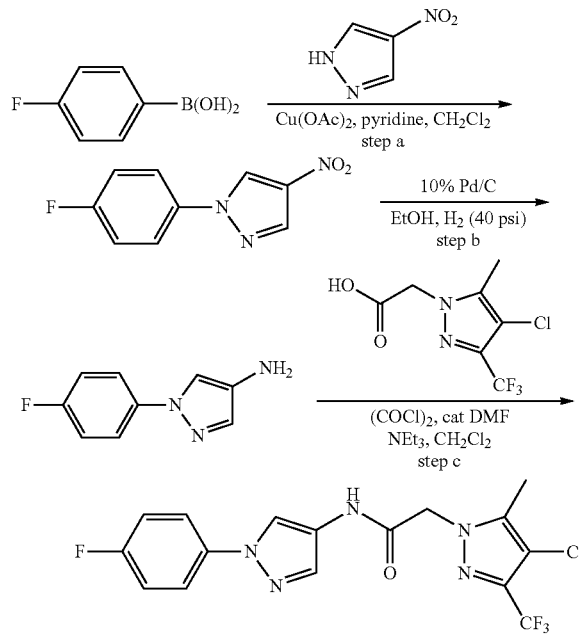

a) A mixture of 4-fluorobenzeneboronic acid (2.47 g, 17.7 mmol), 4-nitro-1H-pyrazole (1.00 g, 8.84 mmol), copper (II) acetate (2.41 g, 13.3 mmol) and pyridine (2.86 mL, 35.4 mmol) in CH$_2$Cl$_2$ (40 mL) was stirred at room temperature overnight. The reaction mixture was filtered and diluted with water (40 mL). The organic layer was separated, dried over anhydrous sodium sulfate, concentrated in vacuo, and purified by flash chromatography (SiO$_2$, 0-20% EtOAc/hexanes gradient elution) to give 1-(4-fluorophenyl)-4-nitropyrazole as a white solid (0.820 g, 22%).

b) A mixture of 1-(4-fluorophenyl)-4-nitropyrazole (0.820 g, 3.96 mmol) and 10% Pd/C (0.133 g, 50% wet by wt) in EtOH (50 mL) was fitted onto a Parr apparatus and agitated under H$_2$ at 40 psi for 40 min. The reaction mixture was then filtered through filter paper. The filtrate was collected and concentrated in vacuo to give 1-(4-fluorophenyl)pyrazol-4-amine as an oil (0.675 g, 96%).

c) To a mixture of 2-[4-chloro-3-methyl-5-(trifluoromethyl)pyrazol-1-yl]acetic acid (0.150 g, 0.62 mmol) in CH$_2$Cl$_2$ (2 mL) was added oxalyl chloride (0.15 mL, 1.75 mmol) and DMF (1 drop). The mixture was stirred for 30 min at room temperature and was then concentrated in vacuo. The solid obtained was transferred to another flask containing 1-(4-fluorophenyl)pyrazol-4-amine (0.080 g, 0.45 mmol) and NEt$_3$ (0.25 mL, 1.8 mmol) in CH$_2$Cl$_2$ (3 mL). The mixture was stirred for 30 min at room temperature, treated with water (50 mL), and extracted with ethyl acetate (50 mL). The organic layer was separated, dried over anhydrous sodium sulfate, concentrated in vacuo, and purified by flash chromatography (SiO$_2$, 0-50% EtOAc/hexanes gradient elution) to give the title compound as a white solid (0.084 g, 47%). $^1$H NMR (400 MHz CDCl$_3$) δ 8.40 (s, 1H), 7.71 (s, 1H), 7.69 (m, 2H), 7.19 (dd, J=8.4, 8.4 Hz, 2H), 5.07 (s, 2H), 2.34 (s, 3H); MS: (ES) m/z calculated for C$_{16}$H$_{12}$ClF$_4$N$_5$O [M+H]$^+$ 402.0, found 402.0.

Example 23

Synthesis of 2-[4-chloro-5-methyl-3-(trifluoromethyl)pyrazol-1-yl]-N-[1-(4-fluorophenyl)pyrazol-4-yl]-N-methyl-acetamide

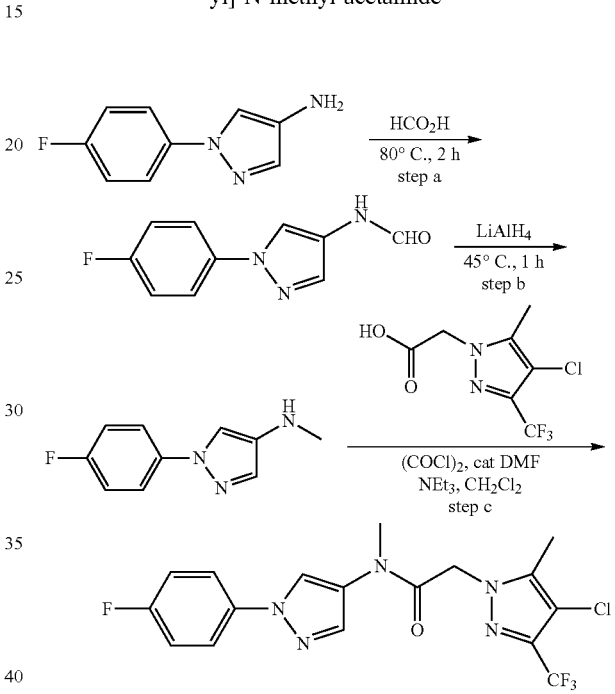

a) A solution of 1-(4-fluorophenyl)pyrazol-4-amine (0.59 g, 3.3 mmol) in formic acid (15 mL) was heated at 80° C. for 2 h. The reaction mixture was cooled to room temperature, concentrated in vacuo, and purified by flash chromatography (SiO$_2$, 0-100% EtOAc/CH$_2$Cl$_2$ gradient elution) to give N-[1-(4-fluorophenyl)pyrazol-4-yl]formamide (0.490 g, 71%).

b) A mixture of N-[1-(4-fluorophenyl)pyrazol-4-yl]formamide (0.275 g, 1.33 mmol) and LiAlH$_4$ (1.33 mL, 2.66 mmol, 2 M in THF) in THF (5 mL) was heated at 45° C. for 1 h. The reaction mixture was cooled to room temperature and diluted with 5 mL of concentrated ammonium hydroxide and 80 mL of 20% MeOH/CH$_2$Cl$_2$. The organic layer was separated, dried over anhydrous sodium sulfate, filtered, concentrated in vacuo, and purified by flash chromatography (SiO$_2$, 0-100% EtOAc/CH$_2$Cl$_2$ gradient elution) to give 1-(4-fluorophenyl)-N-methylpyrazol-4-amine as an oil (0.23 g, 90%).

c) To a solution of 2-[4-chloro-3-methyl-5-(trifluoromethyl)pyrazol-1-yl]acetic acid (0.070 g, 0.29 mmol) in CH$_2$Cl$_2$ (2 mL) was added oxalyl chloride (0.10 mL, 1.16 mmol) and DMF (1 drop). The mixture was stirred for 30 min at room temperature and concentrated in vacuo. The solid obtained was transferred to another flask containing 1-(4-fluorophenyl)-N-methylpyrazol-4-amine (0.056 g, 0.29 mmol) and NEt₃ (0.20 mL, 1.4 mmol) in CH₂Cl₂ (3 mL). The reaction mixture was stirred for 30 min at room temperature, quenched with water (50 mL), and extracted with ethyl acetate (50 mL). The organic layer was separated, dried over anhydrous sodium sulfate, concentrated in vacuo, and purified by flash chromatography (SiO₂, 0-50% EtOAc/CH₂Cl₂ gradient elution) to give the title compound (0.045 g, 37%). ¹H NMR (400 MHz, CDCl₃) δ 8.01 (s, 1H), 7.70 (s, 1H), 7.64 (m, 2H), 7.17 (dd, J=8.4, 8.4 Hz, 2H), 4.80 (s, 2H), 3.28 (s, 3H); MS: (ES) m/z calculated for C₁₇H₁₄ClF₄N₅O [M+H]⁺ 416.1, found 416.1.

Example 24

Synthesis of N-[1-(4-chlorophenyl)-5-isopropylpyrazol-4-yl]-2-[2-methyl-4-(trifluoromethyl)imidazol-1-yl]propanamide

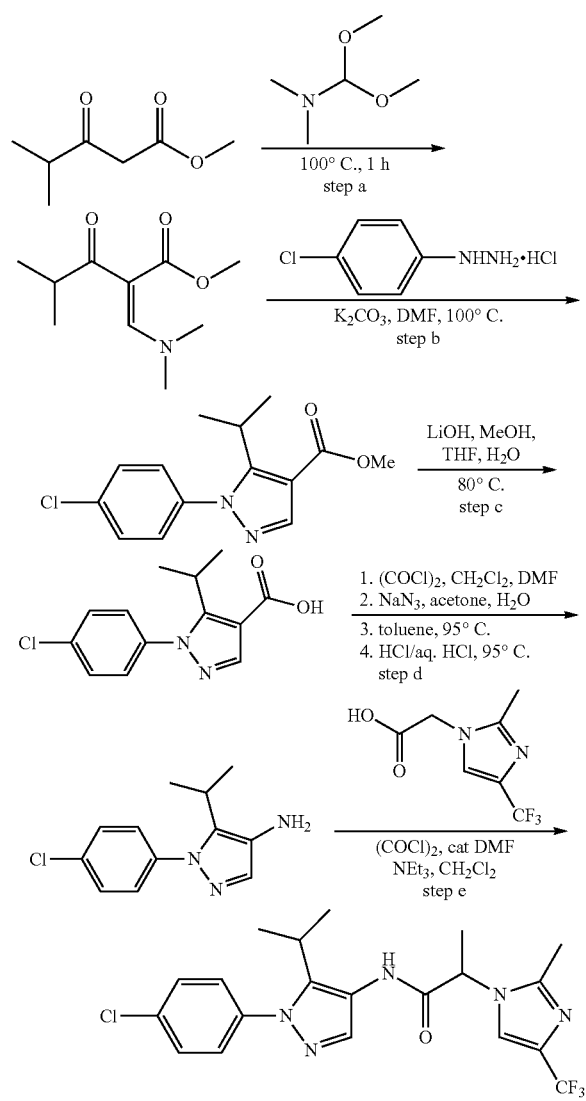

a) A mixture of methyl 4-methyl-3-oxovalerate (15.0 g, 104 mmol) and N,N-dimethylfomamide dimethyl acetal (69 g, 580 mmol) was heated at 100° C. for 1 h. The reaction mixture was cooled to room temperature, concentrated in vacuo, and azeotroped with toluene. The obtained oily residue was used without further purification.

b) A mixture of the intermediate from step a (approx. 104 mmol), 4-chlorophenylhydrazine hydrochloride (18.6 g, 104 mmol), and K₂CO₃ (28.8 g, 208 mmol) in DMF (150 mL) was heated at 100° C. for 1 h. The reaction mixture was cooled to room temperature, diluted with saturated aqueous NH₄Cl (400 mL), and extracted with EtOAc (600 mL). The organic layer was separated, dried over anhydrous sodium sulfate, concentrated in vacuo, and purified by flash chromatography (SiO₂, 0-10% EtOAc/CH₂Cl₂ gradient elution) to give methyl 1-(4-chlorophenyl)-5-isopropyl-pyrazole-4-carboxylate (26.0 g, 90%).

c) A mixture of methyl 1-(4-chlorophenyl)-5-isopropyl-pyrazole-4-carboxylate (26.0 g, 96.7 mmol) and lithium hydroxide monohydrate (10.0 g, 238 mml) in MeOH (60 mL), THF (60 mL), and H₂O (30 mL) was heated at 80° C. for 3 h. The reaction mixture was cooled to room temperature, acidified with 1 N aqueous HCl, and extracted with EtOAc (600 ml). The organic layer was separated, dried over anhydrous sodium sulfate, and concentrated in vacuo to yield 1-(4-chlorophenyl)-5-isopropylpyrazole-4-carboxylic acid (24.0 g, 97%).

d) To a solution of 1-(4-chlorophenyl)-5-isopropylpyrazole-4-carboxylic acid (10.0 g, 37.78 mmol) in CH₂Cl₂ (150 mL) was added oxalyl chloride (9.90 mL, 113.6 mmol) and DMF (0.15 mL). The mixture was stirred for 2 h at room temperature, concentrated in vacuo, and re-dissolved into 100 mL of acetone. The obtained acyl chloride solution was added portionwise to another flask containing NaN₃ (12.31 g, 190 mmol) in H₂O (100 mL) at 0° C. After 10 min, The reaction mixture was diluted with brine (300 mL) and extracted with EtOAc (500 mL). The organic layer was separated, dried over anhydrous sodium sulfate, and concentrated in vacuo. The obtained acyl azide was diluted in 150 mL of toluene and heated at 95° C. until no more gas evolution occurred (approx. 1.5 h). The reaction mixture was cooled to rt and treated with 100 mL of dioxane and 300 mL of 1 M aqueous HCl. The resulting two-phase solution was heated to 95° C. After approx. 2.5 h, the reaction mixture was cooled to rt, made basic with dilute NH₄OH, and extracted with EtOAc (500 ml). The organic layer was separated, dried over anhydrous sodium sulfate, concentrated in vacuo, and purified by flash chromatography (SiO₂, 0-100% EtOAc/CH₂Cl₂ gradient elution) to yield 1-(4-chlorophenyl)-5-isopropylpyrazol-4-amine (5.7 g, 64%).

e) To a solution of 2-[2-methyl-4-(trifluoromethyl)imidazole-1-yl]propanoic acid (0.035 g, 0.16 mmol) in CH₂Cl₂ (2 mL) was added oxalyl chloride (0.050 mL, 0.58 mmol) and DMF (1 drop). The mixture was stirred for 30 min at room temperature and concentrated in vacuo. The residue obtained was transferred to another flask containing 1-(4-chlorophenyl)-5-isopropylpyrazol-4-amine (0.035 g, 0.15 mmol) and NEt₃ (0.060 mL, 0.43 mmol) in CH₂Cl₂ (3 mL). After stirring for 30 min at room temperature, the reaction was quenched with saturated aqueous NaHCO₃ (30 mL) and the mixture was extracted with ethyl acetate (50 mL). The organic layer was separated, dried over anhydrous sodium sulfate, concentrated in vacuo, and purified by reverse phase HPLC (C18 column, acetonitrile-H₂O with 0.1% TFA as eluent) to afford the TFA salt of the titled compound (0.050 g, 57%) as a white solid. ¹H NMR (TFA salt) (400 MHz, CD3OD) δ 7.88 (m, 1H), 7.57 (m, 3H), 7.40 (m, 1H), 5.22 (q, J=7.2 Hz, 1H), 3.00 (septet, J=7.1 Hz, 2H), 2.51 (s, 3H), 1.83 (d, J=7.6 Hz, 3H), 1.19 (m, 6H); MS: (ES) m/z calculated for $C_{20}H_{21}Cl_1F_3N_5O$ [M+H]$^+$ 440.1, found 440.1.

Example 25

Synthesis of N-[2-(4-Chlorophenyl)-3-isopropyl-imidazol-4-yl]-2-[2-methyl-4-(trifluoromethyl)imidazol-1-yl]propanamide

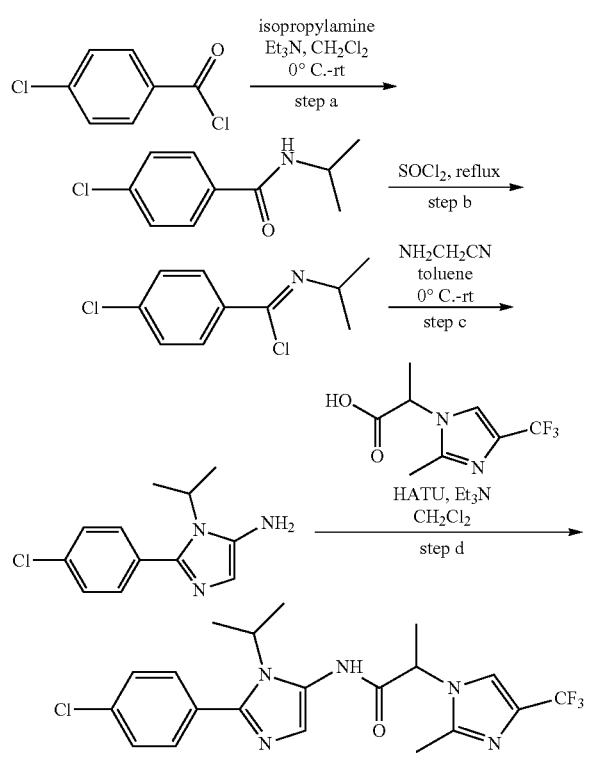

a) To a solution of 4-chlorobenzoyl chloride (1.75 g, 10.0 mmol) in CH$_2$Cl$_2$ (20 mL) was added Et$_3$N (3 mL, 21 mmol) and propan-2-amine (1.3 mL, 15 mmol) at 0° C. The resulting mixture was stirred overnight at room temperature before it was diluted with saturated aqueous NaHCO$_3$ solution (30 mL) and extracted with EtOAc (50 mL). The organic layer was separated, washed with brine, dried (Na$_2$SO$_4$), filtered, and concentrated in vacuo. The crude material was used directly in the next step.

b) A mixture of the crude product from step a and thionyl chloride (20 mL) was refluxed overnight. After cooling to room temperature, the reaction mixture was concentrated in vacuo. The crude material was used directly in the next step.

c) To a stirred solution of (1Z)-4-chloro-N-isopropyl-benzimidoyl chloride (1.00 g, 4.6 mmol) in toluene (2 mL) was added 2-aminoacetonitrile (0.26 g, 4.6 mmol), at 0° C. The resulting solution was stirred at room temperature overnight before before it was diluted with saturated aqueous NaHCO$_3$ solution (10 mL) and extracted with EtOAc (20 mL). The organic layer was subsequently washed with brine, dried (Na$_2$SO$_4$), filtered, and concentrated in vacuo. Purification by flash chromatography (SiO$_2$, 100% EtOAc-20% MeOH/EtOAc) gave the desired product (0.50 g, 2.1 mmol, 45% yield).

d) A mixture of 2-(4-chlorophenyl)-3-isopropyl-imidazol-4-amine (0.10 g, 0.43 mmol), 2-[2-methyl-4-(trifluoromethyl)imidazol-1-yl]propanoic acid (0.09 g, 0.43 mmol), HATU (0.16 g, 0.43 mmol), and Et$_3$N (200 μL, 1.4 mmol) in CH$_2$Cl$_2$ (1 mL) was stirred at room temperature for 30 min. The reaction mixture was then diluted with 10 mL of saturated aqueous NaHCO$_3$ solution and extracted with EtOAc. The organic layer was subsequently washed with brine, dried (Na$_2$SO$_4$), filtered, and concentrated in vacuo. The resulting crude product was purified by flash chromatography (SiO$_2$, 100% EtOAc-30% MeOH/EtOAc) to afford the titled compound as a white solid (0.046 g, 0.10 mmol, 23% yield). $^1$H NMR (400 MHz, CDCl$_3$) 7.52 (s, 1H), 7.44 (d, J=8.0 Hz, 2H), 7.32 (d, J=8.0 Hz, 2H), 7.07 (s, 1H), 5.18 (q, J=7.1 Hz, 1H), 4.36 (q, J=7.0 Hz, 1H), 2.42 (s, 3H), 1.78 (d, J=7.1 Hz, 3H), 1.33 (d, J=7.0 Hz, 6H). MS: (ES) m/z calculated for $C_{20}H_{21}ClF_3N_5O$ [M+H]$^+$ 440.1, found 440.4.

Example 26

Synthesis of (2S)—N-[1-(4-chlorophenyl)-5-cyclobutyl-pyrazol-4-yl]-2-[2-methyl-4-(trifluoromethyl)imidazol-1-yl]propanamide and (2R)—N-[1-(4-chlorophenyl)-5-cyclobutyl-pyrazol-4-yl]-2-[2-methyl-4-(trifluoromethyl)imidazol-1-yl]propanamide

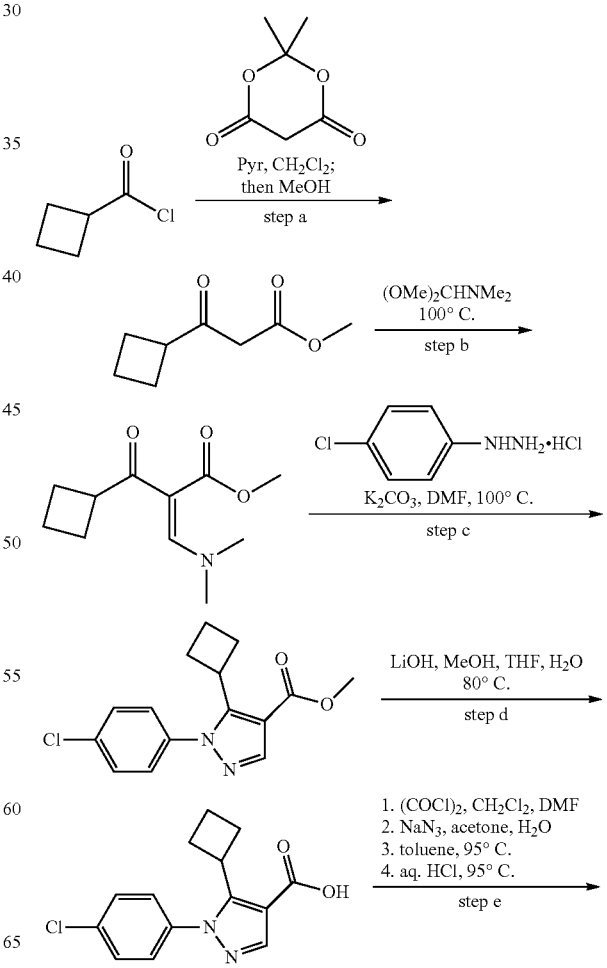

-continued

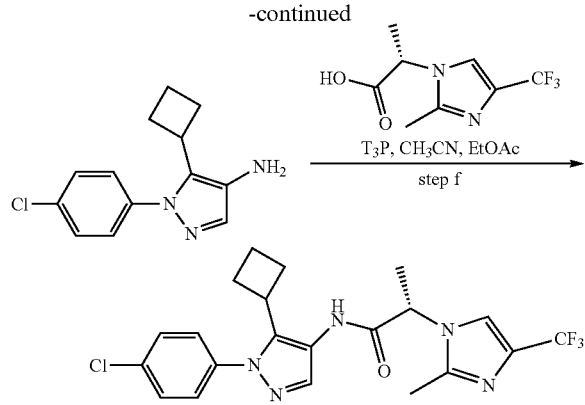

a) Pyridine (20.46 mL, 253 mmol) was added to a solution of cyclobutanecarboxylic acid chloride (10.0 g, 84.3 mmol) and isopropylidene malonate (12.16 g, 84.3 mmol) in $CH_2Cl_2$ (100 mL) at 0° C. and the mixture was stirred at room temperature for 1.5 h. Methanol (100 mL) was then added and the resulting mixture was stirred at reflux for 3 h, cooled to room temperature and partitioned between aqueous HCl (1 M, 200 mL) and EtOAc (500 mL). The organic layer was separated, dried over anhydrous sodium sulfate, concentrated in vacuo and purified by flash chromatography ($SiO_2$, 0-20% EtOAc/hexanes gradient elution) to give methyl 3-cyclobutyl-3-oxo-propanoate (11.6 g, 88% yield).

b) A mixture of methyl 3-cyclobutyl-3-oxo-propanoate (5.8 g, 37.2 mmol) and N,N-dimethylformamide dimethyl acetal (25 g, 210 mmol) was stirred at 100° C. for 1 h. After cooling to room temperature the mixture was concentrated in vacuo to give an oily residue that was directly carried to the next step.

c) A mixture of the intermediate (~37.2 mmol) obtained in step b, 4-chlorophenylhydrazine hydrochloride (6.67 g, 37.2 mmol), and $K_2CO_3$ (10.3 g, 74.4 mmol) in DMF (50 mL) was stirred at 100° C. for 1 h. After cooling to room temperature the mixture was diluted with aqueous HCl (200 mL) and extracted with EtOAc (500 mL). The organic layer was separated, dried over anhydrous sodium sulfate, concentrated in vacuo and purified by flash chromatography ($SiO_2$, 0-10% EtOAc/$CH_2Cl_2$ gradient elution) to give methyl 1-(4-chlorophenyl)-5-cyclobutyl-pyrazole-4-carboxylate (8.3 g, 76% yield).

d) A mixture of methyl 1-(4-chlorophenyl)-5-cyclobutyl-pyrazole-4-carboxylate (8.3 g, 28.5 mmol) and lithium hydroxide monohydrate (3.6 g, 85.6 mmol) in MeOH (25 mL), THF (25 mL), and $H_2O$ (12 mL) was stirred at 80° C. for 1 h. After cooling to room temperature the mixture was acidified with 1 M aqueous HCl and extracted with EtOAc (400 mL). The organic layer was separated, dried over anhydrous sodium sulfate, and concentrated in vacuo to yield 1-(4-chlorophenyl)-5-cyclobutyl-pyrazole-4-carboxylic acid (6.92 g, 87% yield).

e) To a mixture of 1-(4-chlorophenyl)-5-cyclobutyl-pyrazole-4-carboxylic acid (4.0 g, 14.4 mmol) in $CH_2Cl_2$ (100 mL) was added oxalyl chloride (3.78 mL, 43.4 mmol) and DMF (0.06 mL). After 2 h at room temperature, the reaction mixture was concentrated in vacuo, re-dissolved in 40 mL of acetone, and added to a 0° C. solution of $NaN_3$ (3.75 g, 57.8 mmol) in $H_2O$ (40 mL). Brine (150 mL) and EtOAc (350 mL) were then added. The organic layer was separated, dried over anhydrous sodium sulfate and concentrated in vacuo. The residue was stirred in 100 mL of toluene at 95° C. for 1 h, cooled to room temperature, and then treated with 150 mL of 6 M aqueous HCl at 110° C. for 1 h. After cooling to room temperature the mixture was basified with dilute $NH_4OH$ and extracted with EtOAc (500 mL). The organic layer was separated, dried over anhydrous sodium sulfate, concentrated in vacuo, and purified by flash chromatography ($SiO_2$, 0-100% EtOAc/$CH_2Cl_2$ gradient elution) to yield 1-(4-chlorophenyl)-5-cylocbutyl-pyrazol-4-amine (2.9 g, 81% yield).

f) A mixture of (2S)-2-[2-methyl-4-(trifluoromethyl)imidazole-1-yl]propanoic acid (0.046 g, 0.21 mmol), 1-(4-chlorophenyl)-5-cylocbutyl-pyrazol-4-amine (0.046 g, 0.18 mmol) and pyridine (0.072 mL, 0.92 mmol) in $CH_3CN$ (1 mL) and EtOAc (1 mL) at 0° C. was treated with 1-propylphosphonic acid cyclic anhydride (50% in EtOAc, 0.24 mL, 0.4 mmol) for 15 min at 0° C., then quenched with 0.5 M aq. HCl (10 mL), neutralized with saturated aqueous $NaHCO_3$ (30 mL), and extracted with ethyl acetate (100 mL). The organic layer was collected, dried over anhydrous sodium sulfate, concentrated in vacuo, and purified by reverse phase HPLC (C18 column, acetonitrile-$H_2O$ with 0.1% TFA as eluent) to afford the TFA salt of the titled compound. It was then converted to the free form by treating with saturated aqueous $NaHCO_3$ followed by EtOAc extraction to afford the titled compound (0.055 g, 65% yield). $^1$H NMR (400 MHz, $CDCl_3$) δ 7.93 (s, 1H), 7.42 (m, 3H), 7.27 (m, 3H), 4.92 (q, J=7.3 Hz, 1H), 3.56 (m, 1H), 2.49 (s, 3H), 1.62-1.96 (m, 9H); MS: (ES) m/z calculated for $C_{21}H_{21}ClF_3N_5O$ [M+H]$^+$ 452.1, found 452.1. Chiral HPLC (Regis Pack CLA-1, cat #793104, 25 cm×4.6 mm, 5 micron; eluent: 0.1% diethylamine/IPA, 0.7 ml/min) analysis of the product showed an enantiomeric ratio of 48:1. The (S)-enantiomer (major) had a retention time of 6.8 min, and the (R)-enantiomer (minor) had a retention time of 5.2 min.

Example 27

This example illustrates the evaluation of the biological activity associated with compounds of interest of the invention.

Materials and Methods

A. Cells

1. CCR1 Expressing Cells a) THP-1 Cells

THP-1 cells were obtained from ATCC (TIB-202) and cultured as a suspension in RPMI-1640 medium supplemented with 2 mM L-glutamine, 1.5 g/L sodium bicarbonate, 4.5 g/L glucose, 10 mM HEPES, 1 mM sodium pyruvate, 0.05% 2-mercaptoethanol and 10% FBS. Cells were grown under 5% $CO_2$/95% air, 100% humidity at 37° C. and subcultured twice weekly at 1:5 (cells were cultured at a density range of $2×10^5$ to $2×10^6$ cells/mL) and harvested at $1×10^6$ cells/mL. THP-1 cells express CCR1 and can be used in CCR1 binding and functional assays.

2. Chemotaxis Assays

Chemotaxis assays were performed using 5 μm pore polycarbonate, polyvinylpyrrolidone-coated filters in 96-well chemotaxis chambers (Neuroprobe; Gaithersburg, Md.) using chemotaxis buffer (Hank's balanced salt solution (HBSS) and 1% FBS). CCR1 chemokine ligands (i.e., MIP-1α, CCL15/Leukotactin; R&D Systems; Minneapolis, Minn.) are use to evaluate compound mediated inhibition of CCR1 mediated migration. Other chemokines (i.e., SDF-1α; R&D Systems; Minneapolis, Minn.) are used as specificity controls. The lower chamber was loaded with 29 μl of chemokine (i.e., 0.1 nM CCL15/Leukotactin) and varying amounts of compound; the top chamber contained 100,000 THP-1 or monocyte cells in 20 μl. The chambers were incubated 1-2 hours at 37° C., and the number of cells in the lower chamber quantified either by direct cell counts in five high powered fields per well or by the CyQuant assay (Molecular Probes), a fluorescent dye method that measures nucleic acid content and microscopic observation.

B. Identification of Inhibitors of CCR1

One of the primary functions of chemokines is their ability to mediate the migration of chemokine receptor-expressing cells, such as white blood cells. To confirm that a compound of interest inhibited not only CCR1 specific binding and signaling (at least as determined by calcium mobilization assays), but also CCR1 mediated migration, a chemotaxis assay was employed. THP-1 myelomonocytic leukemia cells, which resemble monocytes, as wells as freshly isolated monocytes, were used as targets for chemoattraction by CCR1 chemokine ligands (i.e., MIP-1α, CCL15/leukotactin). Cells were placed in the top compartment of a microwell migration chamber, while MIP-1α (or other potent CCR1 chemokine ligand) and increasing concentrations of a compound of interest was loaded in the lower chamber. In the absence of inhibitor, cells will migrate to the lower chamber in response to the chemokine agonist; if a compound inhibited CCR1 function, then the majority of cells will remain in the upper chamber. To ascertain a compound of interest's affinity for CCR1 as well as to confirm its ability to inhibit CCR1 mediated cell migration, inhibitory activity was titered over a $1\times10^{-10}$ to $1\times10^{-4}$ M range of compound concentrations in this chemotaxis assay. In this assay, the amount of compound was varied; while cell number and chemokine agonist concentrations were held constant. After the chemotaxis chambers were incubated 1-2 hours at 37° C., the responding cells in the lower chamber were quantified by labeling with the CyQuant assay (Molecular Probes), a fluorescent dye method that measures nucleic acid content, and by measuring with a Spectrafluor Plus (Tecan). The computer program Prism from GraphPad, Inc. (San Diego, Ca) was used to calculate $IC_{50}$ values. $IC_{50}$ values are those compound concentrations required to inhibit the number of cells responding to a CCR1 agonist by 50%.

1. In Vivo Efficacy a) Rabbit Model of Destructive Joint Inflammation

A rabbit LPS study was conducted essentially as described in Podolin, et al. *J. Immunol.* 169(11):6435-6444 (2002). Female New Zealand rabbits (approximately 2 kilograms) were treated intra-articularly in both knees with LPS (10 ng). *The compound of interest, for example* 1.016, (formulated in 1% methocel) or vehicle (1% methocel) was dosed orally at a 5 ml/kg dose volume at two times (2 hours before the intra-articular LPS injection and 4 hours after the intra-articular LPS injection). Sixteen hours after the LPS injection, knees were lavaged and cells counts were performed. Beneficial effects of treatment were determined by reduction in the number of inflammatory cells recruited to the inflamed synovial fluid of the knee joints. Treatment with the compound of interest resulted in a significant reduction in recruited inflammatory cells.

b) Evaluation of a Compound of Interest in a Rat Model of Collagen Induced Arthritis A 17 day developing type II collagen arthritis study is conducted to evaluate the effects of a compound of interest on arthritis induced clinical ankle swelling. Rat collagen arthritis is an experimental model of polyarthritis that has been widely used for preclinical testing of numerous anti-arthritic agents (see Trentham, et al., *J. Exp. Med.* 146(3): 857-868 (1977), Bendele, et al., *Toxicologic Pathol.* 27:134-142 (1999), Bendele, et al., *Arthritis Rheum.* 42:498-506 (1999)). The hallmarks of this model are reliable onset and progression of robust, easily measurable polyarticular inflammation, marked cartilage destruction in association with pannus formation and mild to moderate bone resorption and periosteal bone proliferation.

Female Lewis rats (approximately 0.2 kilograms) are anesthetized with isoflurane and injected with Freund's Incomplete Adjuvant containing 2 mg/mL bovine type II collagen at the base of the tail and two sites on the back on days 0 and 6 of this 17 day study. A compound of interest is dosed daily in a sub-cutaneous manner from day 0 till day 17 at a efficacious dose. Caliper measurements of the ankle joint diameter are taken, and reduced joint swelling is taken as a measure of efficacy.

Murine Model of Dermatological Disease

Compounds of the invention can be assessed in the murine model of dermal delayed type hypersensitivity induced by oxazolone. Briefly, 8-10 week old BALB/c mice are sensitized topically with a 1% solution of oxazolone dissolved in ethanol on their shaved abdomens on day 0. On day 6 post sensitization mice are dosed orally with either vehicle or increasing doses of a compound of the invention immediately prior to and 4 hours following a topical challenge with a 0.5% solution of oxazolone in ethanol on the right ear. The following day (day 7), ear thicknesses are measured using caliper measurements. Animals treated with compound have significantly reduced ear swelling compared to vehicle treated controls indicating a compound mediated decrease in oxazolone induced dermal hypersensitivity.

Murine Asthma Model

Compounds of the invention can be assessed in the murine model of allergic asthma. Asthma is induced in 8-10 week old BALB/c mice by sensitizing mice with OVA in Alum adjuvant on days 0 and 10. On day 20 mice are challenged with OVA in PBS intranasally to elicit airway inflammation. Groups of mice are either treated with vehicle, or increasing doses of a compound of the invention starting on day 20 and lasting until day 23. Animals are analyzed at day 23 after the intranasal OVA challenge for cellular infiltrates in bronchoalveolar lavage (BAL). A significant reduction in BAL leukocyte numbers relative to vehicle treated mice indicates the compound is effective in this model.

Murine Model of Systemic Lupus Erythematosus

This example describes a procedure to evaluate efficacy of CCR1 antagonists for treatment of Systemic Lupus Erythematosus (SLE). Female NZB/W FI mice spontaneously develop an SLE-like pathology commencing at 6 months of age that is characterized by proteinuria, serum autoantibodies, glomerulonephritis, and eventually death. Three series of NZB/W FI mouse groups comprising 20 mice per group are tested for efficacy of CCR1 antagonist as follows: One series of mice additionally receives phosphate buffered saline (PBS) and Tween 0.5% i.p. soon after weaning, and thereafter at varying dosing schedules. A second series consists of groups of mice receiving different doses of the CCR1 antagonist given either intra-peritoneally, intra-venously, sub-cutaneously, intramuscularly, orally, or via any other mode of administration soon after weaning, and thereafter at varying dosing schedules. A third series of mice, serving as positive control, consists of groups treated with anti-IL10 antibodies given soon after weaning, and thereafter at varying dosing schedules. Disease development is monitored in terms of eventual mortality, kidney histology, serum autoantibody levels, and proteinuria.

Murine Model of Cancer

This example describes a procedure to evaluate efficacy of CCR1 antagonists for treatment of malignancy. Normal mouse strains can be transplanted with a variety of well-characterized mouse tumor lines, including a mouse thymoma EL4 which has been transfected with OVA to allow easy evaluation of tumor specific antigen responses following vaccination with OVA. Three series of mouse groups from any of these tumor models are tested for CCR1 antagonist efficacy as follows: One series of mice additionally receives PBS and Tween 0.5% i.p. soon after tumor transplant, and thereafter at varying dosing schedules. A second series consists of groups of mice receiving different doses of the CCR1 antagonist given either intra-peritoneally, intra-venously, sub-cutaneously, intramuscularly, orally, or via any other mode of administration soon after tumor transplant, and thereafter at varying dosing schedules. A third series of mice, serving as positive control, consists of groups treated with either anti-IL4 antibodies, anti-IFNg antibodies, IL4, or TNF, given i.p. soon after tumor transplant, and thereafter at varying dosing schedules. Efficacy is monitored via tumor growth versus regression. In the case of the OVA-transfected EL4 thymoma model, cytolytic OVA-specific responses can be measured by stimulating draining lymph node cells with OVA in vitro, and measuring antigen-specific cytotoxicity at 72 hours.

Murine Model of Psoriasis

This example describes procedures to evaluate the efficacy of CCR1 antagonists in psoriasis. A rodent model of psoriasis can be obtained by intra-venously transferring a population of purified T cells (designated CD45Rbhi T cells) obtained from the spleens of BALB/c mice into immunodeficient recipient CB.17 scid/scid mice. Mice develop signs of redness, swelling, and skin lesions resembling those of human psoriasis in their ear, feet and tail by 8 weeks after transfer. Three series of mouse groups, comprising 10-15 CB.17 scid/scid mice per group, are injected with purified CD45Rbhi T cells. One series of mice additionally receives phosphate buffered saline (PBS) and Tween 0.5% i.p. at the initial cell transfer, and at different dosing schedules thereafter. A second series consists of groups of mice receiving different doses of the CCR1 antagonist given either intra-peritoneally, intra-venously, sub-cutaneously, intra-muscularly, orally, or via any other mode of administration at the initial cell transfer, and at different dosing schedules thereafter. A third series of mice, serving as positive control, consists of groups treated with antibodies to either IL-12, IL-4, IFNg, or TNF, or with cytokine IL-10 at the initial cell transfer, and at different dosing schedules thereafter. Animals are monitored for development of psoriatic-like lesions for 3 months after cell transfer.

Murine Model of Inflammatory Bowel Diseases

The MDR1a-knockout mice, which lack the P-glycoprotein gene, spontaneously develop colitis under specific pathogen-free condition. The pathology in these animals has been characterized as Th1-type T cell-mediated inflammation similar to ulcerative colitis in humans. Disease normally begins to develop at around 8-10 weeks after birth. However the ages at which disease emerges and the ultimate penetrance level often vary considerably among different animal facilities. In a study using the MDR1a-knockout mice, a CCR1 antagonist can be evaluated prophylacticly or therapeutically depending on time of administration. Female mice (n=34) are dosed with a compound of interest as appropriate to the compound eg daily in a sub-cutaneous manner at a efficacious dose. The study is evaluated for IBD associated growth retardation and scoring of anal discharge and irritation. A compound which reduces anal discharge and irritation or inhibits IBD associated growth retardation indicates efficacy of compound in this indication.

Murine Model of Solid Tumors

The mouse RENCA tumor model accurately mimics the progression of human adult renal cell carcinoma specifically with reference to spontaneous metastasis to lungs and serves as a model for solid tumors. Balb/c 6-8 week old female mice are inoculated with approximately 5e5 RENCA cells (mouse renal adenocarcinoma; ATCC cat# CRL-2947) under the kidney capsule and kidney tumor growth is observed over 22 days, with lung metastasis observed as early as day 15. Animals are dosed with either vehicle or a compound of the invention eg daily subcutaneously, from the time of tumor implantation to monitor effects on primary growth, or at a later time (eg day 7) to monitor the compound effect on metastasis. Primary tumor areas are measured twice a week using mechanical calipers. Tumor volumes are calculated by the formula v=pab2/6, where a is the longest diameter and b is the next longest diameter perpendicular to a. A reduction in tumor volume or incidence of metastasis indicates efficacy of compound in this indication.

Murine Model of Inflammation

A method of inducing peritoneal inflammation by the introduction of 3% thioglycolate into the peritoneum is well know in the art. Following the introduction of thioglycolate, a rapid influx of immune cells to the site, primarily CCR1 bearing neutrophils, results in local inflammation at 24 hours. A peritoneal exudate can be sampled, and the cell number and composition can be assessed to determine the anti-inflammatory properties of a compound of interest administered before, during or after the thioglycolate induction.

In Table 1 (below), structures and activity are provided for representative compounds described herein. Activity is provided as follows for the chemotaxis assay as described above: +, 10 μM>$IC_{50}$>100 nM; ++, $IC_{50}$≤100 nM.

TABLE 1

| | | Migration IC50 (nM) |
|---|---|---|
| 1.001 | 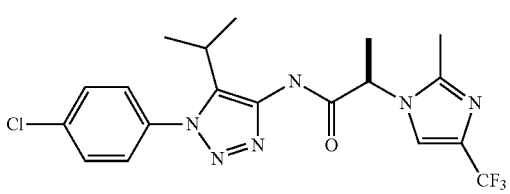 [SMILES: Cc1nc(C(F)(F)F)cn1[C@H](C)C(=O)Nc1nnn(-c2ccc(Cl)cc2)c1C(C)C] | ++ |

TABLE 1-continued
| | | Migration IC50 (nM) |
|---|---|---|
| 1.002 | 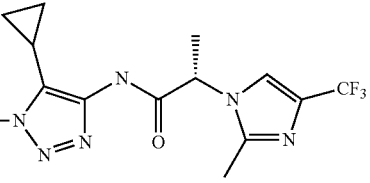 | + |
| 1.003 | 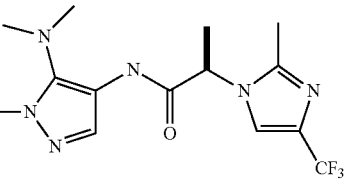 | + |
| 1.004 | 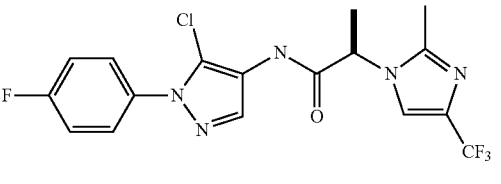 | + |
| 1.005 | 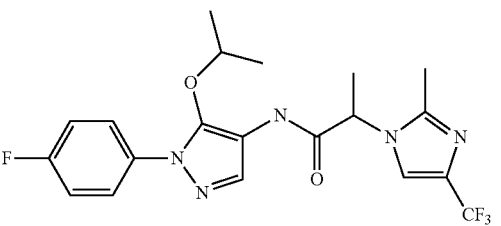 [SMILES: Cc1nc(C(F)(F)F)cn1C(C)C(=O)Nc1cnn(-c2ccc(F)cc2)c1OC(C)C] | + |
| 1.006 | 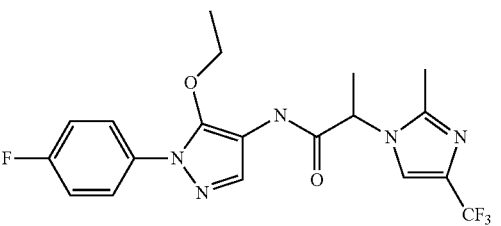 [SMILES: CCOc1c(NC(=O)C(C)n2cc(C(F)(F)F)nc2C)cnn1-c1ccc(F)cc1] | + |
| 1.007 | 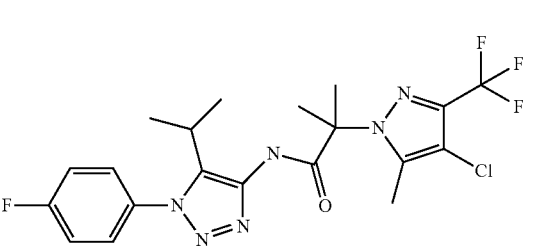 [SMILES: Cc1c(Cl)c(C(F)(F)F)nn1C(C)(C)C(=O)Nc1nnn(-c2ccc(F)cc2)c1C(C)C] | + |
| 1.008 | 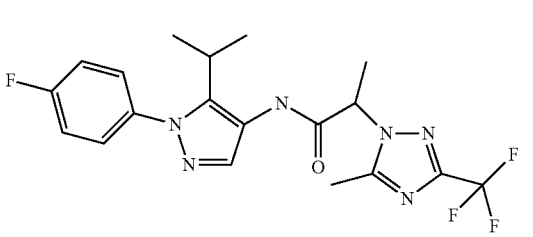 [SMILES: Cc1nc(C(F)(F)F)nn1C(C)C(=O)Nc1cnn(-c2ccc(F)cc2)c1C(C)C] | + |

TABLE 1-continued

| | | Migration IC50 (nM) |
|---|---|---|
| 1.009 | | ++ |
| 1.010 | | ++ |
| 1.011 | | ++ |
| 1.012 | | ++ |
| 1.013 | | + |
| 1.014 | | + |
| 1.015 | | ++ |

TABLE 1-continued

| | | Migration IC50 (nM) |
|---|---|---|
| 1.016 | | ++ |
| 1.017 | | ++ |
| 1.018 | | ++ |
| 1.019 | | ++ |
| 1.020 | | + |
| 1.021 | | + |
| 1.022 | | ++ |

TABLE 1-continued

| | | Migration IC50 (nM) |
|---|---|---|
| 1.023 | | + |
| 1.024 | | + |
| 1.025 | | + |
| 1.026 | | + |
| 1.027 | | + |
| 1.028 | | + |
| 1.029 | | ++ |

What is claimed is:

1. A method of treating CCR1-mediated diseases or conditions, wherein said CCR1-mediated diseases or conditions are selected from the group consisting of transplant rejection, dermatitis, inflammatory bowel disease, asthma, Alzheimer's disease, psoriasis, encephalomyelitis, rheumatoid arthritis, multiple sclerosis, multiple myeloma, osteoporosis, and leukemia comprising administering to a subject in need thereof a therapeutically effective amount of the compound represented by the structure:

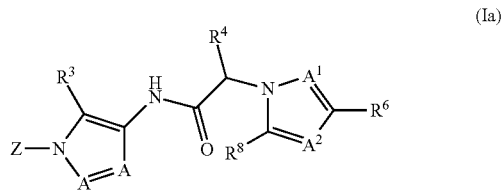

wherein
each A is independently selected from the group consisting of N and CH;
$A^1$ is N or $C(R^5)$;
$A^2$ is N or $C(R^7)$;
Z is phenyl and is optionally substituted with 1-3 $R^a$;
$R^3$ is a member selected from the group consisting of halogen, $C_{1-8}$alkyl, $C_{3-8}$ cycloalkyl, $C_{1-8}$ haloalkyl, —$OR^a$, —$NR^aR^b$, and phenyl, and wherein the alkyl, cycloalkyl, and phenyl portions of $R^3$ are optionally further substituted with 1-3 $R^3$;
$R^4$ is a member selected from the group consisting of H and $C_{1-8}$ alkyl;
$R^5$, $R^6$, $R^7$ and $R^8$ are each independently selected from the group consisting of H, halogen, $C_{1-8}$ alkyl, and $C_{1-8}$ haloalkyl optionally further substituted with 1-3 $R^a$; and optionally, $R^4$ and $R^5$, are connected to form an additional 5- or 6-membered ring which is saturated, unsaturated or aromatic having carbon atom ring vertices;
each $R^a$ and $R^b$ is independently selected from the group consisting of hydrogen, hydroxyl, halogen, cyano, $C_{1-8}$ alkyl, $C_{1-8}$ alkoxy, $C_{1-8}$ haloalkyl, $C_{3-6}$ cycloalkyl, $C_{3-6}$ cycloalkylalkyl, amino, $C_{1-8}$ alkylamino, di $C_{1-8}$ alkylamino, carboxamide, carboxy $C_{1-4}$ alkyl ester, carboxylic acid, and —$SO_2$—$C_{1-8}$ alkyl;
or a pharmaceutically acceptable salt thereof.

2. A method in accordance with claim 1, wherein said CCR1-mediated disease or condition is selected from the group consisting of transplant rejection, dermatitis, inflammatory bowel disease, asthma, Alzheimer's disease, psoriasis, and encephalomyelitis.

3. A method in accordance with claim 1, wherein said CCR1-mediated disease or condition is selected from the group consisting of rheumatoid arthritis, multiple sclerosis, multiple myeloma and osteoporosis.

4. A method in accordance with claim 1, wherein said administering is oral, parenteral, rectal, transdermal, sublingual, nasal or topical.

5. A method in accordance with claim 1, wherein said compound is administered in combination with an anti-inflammatory agent, analgesic agent, an anti-proliferative agent, a metabolic inhibitor, a leukocyte migration inhibitor or an immuno modulator.

6. A method in accordance with claim 1, wherein said CCR1-mediated disease or condition is rheumatoid arthritis.

7. A method in accordance with claim 1, wherein said CCR1-mediated disease or condition is selected from the group consisting of multiple myeloma and leukemia.

8. A method of treating CCR1-mediated diseases or conditions, wherein said CCR1-mediated diseases or conditions are selected from the group consisting of transplant rejection, dermatitis, inflammatory bowel disease, asthma, Alzheimer's disease, psoriasis, encephalomyelitis, rheumatoid arthritis, multiple sclerosis, multiple myeloma, osteoporosis, and leukemia comprising administering to a subject in need thereof a therapeutically effective amount of a compound selected from the group consisting of:

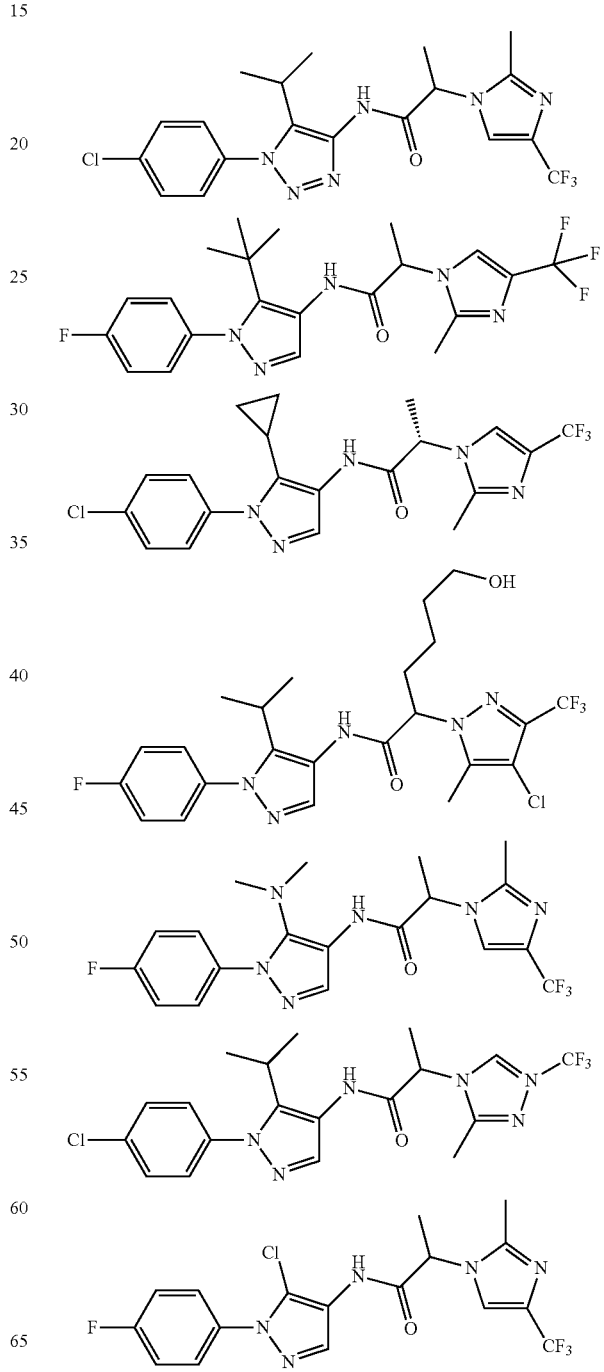

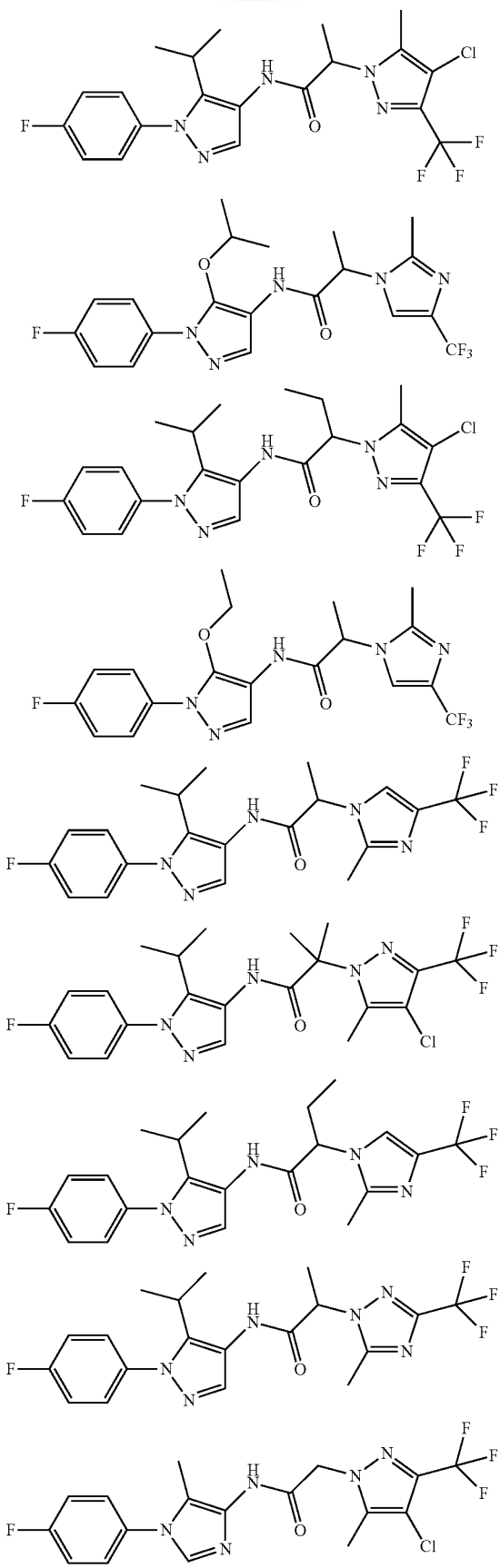
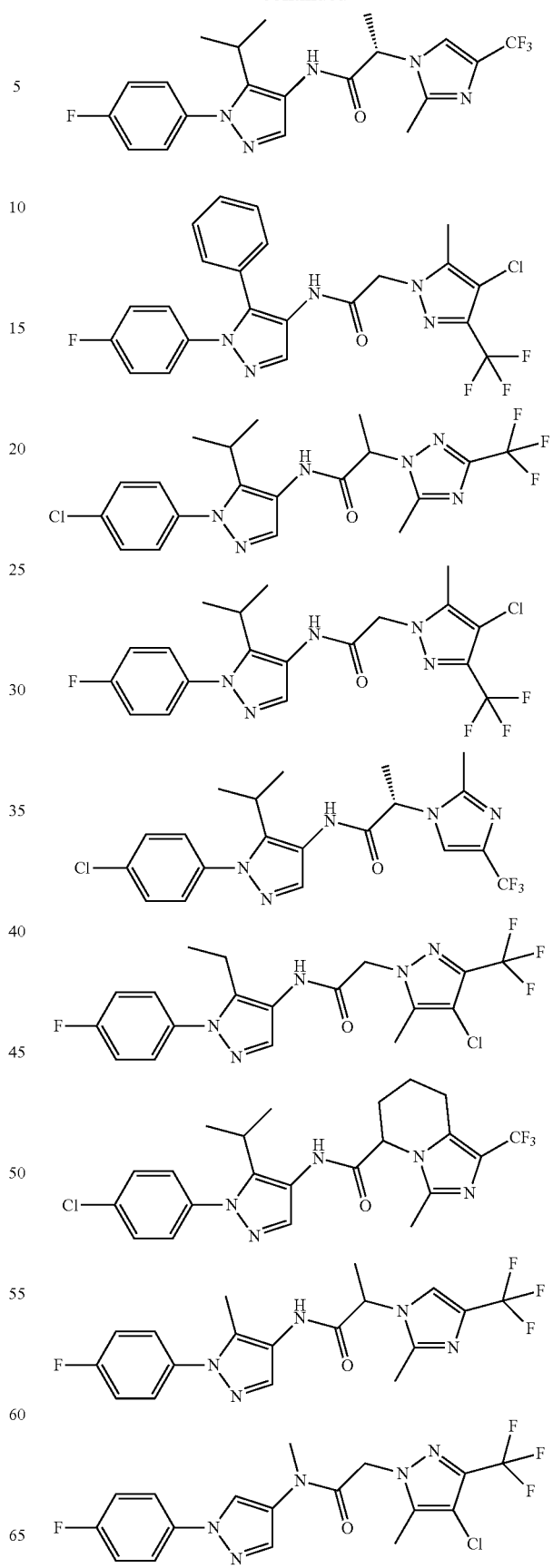

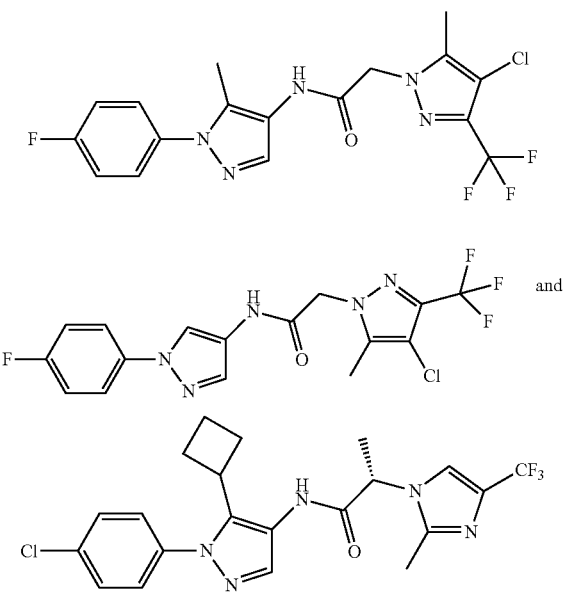

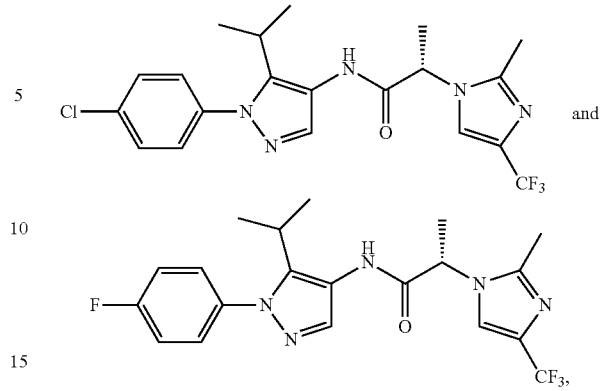

or a pharmaceutically acceptable salt thereof.

14. A method in accordance with claim 12, wherein the compound is selected from the group consisting of:

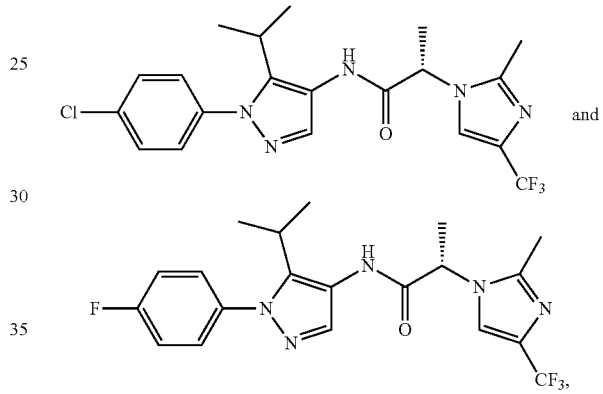

or a pharmaceutically acceptable salt thereof.

9. A method in accordance with claim 8 wherein the compound is:

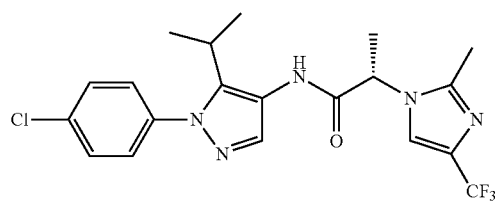 [SMILES: Cc1nc(C(F)(F)F)cn1[C@@H](C)C(=O)Nc1cnn(-c2ccc(Cl)cc2)c1C(C)C]

or a pharmaceutically acceptable salt thereof.

10. A method in accordance with claim 8 wherein the compound is:

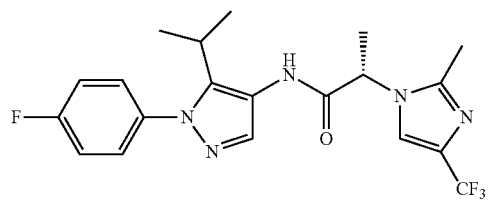 [SMILES: Cc1nc(C(F)(F)F)cn1[C@@H](C)C(=O)Nc1cnn(-c2ccc(F)cc2)c1C(C)C]

or a pharmaceutically acceptable salt thereof.

11. A method in accordance with claim 8, wherein said CCR1-mediated disease or condition is selected from the group consisting of transplant rejection, dermatitis, inflammatory bowel disease, asthma, Alzheimer's disease, psoriasis, encephalomyelitis, rheumatoid arthritis, multiple sclerosis, multiple myeloma and osteoporosis.

12. A method in accordance with claim 8, wherein said CCR1-mediated disease or condition is rheumatoid arthritis.

13. A method in accordance with claim 11, wherein the compound is selected from the group consisting of:

or a pharmaceutically acceptable salt thereof.

15. A method in accordance with claim 8, wherein said administering is oral, parenteral, rectal, transdermal, sublingual, nasal or topical.

16. A method in accordance with claim 8, wherein said compound is administered in combination with an anti-inflammatory agent, an analgesic agent, an anti-proliferative agent, a metabolic inhibitor, a leukocyte migration inhibitor or an immuno modulator.

17. A method of modulating CCR1 function comprising administering to a subject in need thereof a therapeutically effective amount of the compound represented by the structure:

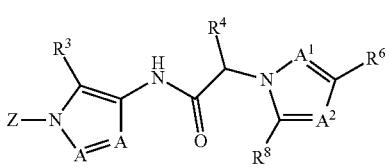

(Ia)

wherein
each A is independently selected from the group consisting of N and CH;
$A^1$ is N or $C(R^5)$;
$A^2$ is N or $C(R^7)$;

Z is phenyl and is optionally substituted with 1-3 $R^a$;

$R^3$ is a member selected from the group consisting of halogen, $C_{1-8}$ alkyl, $C_{3-8}$ cycloalkyl, $C_{1-8}$ haloalkyl, —$OR^a$, —$NR^aR^b$, and phenyl, and wherein the alkyl, cycloalkyl, and phenyl portions of $R^3$ are optionally further substituted with 1-3 $R^a$;

$R^4$ is a member selected from the group consisting of H and $C_{1-8}$ alkyl;

$R^5$, $R^6$, $R^7$ and $R^8$ are each independently selected from the group consisting of H, halogen, $C_{1-8}$ alkyl, and $C_{1-8}$ haloalkyl optionally further substituted with 1-3 $R^a$; and optionally, $R^4$ and $R^5$, are connected to form an additional 5- or 6-membered ring which is saturated, unsaturated or aromatic having carbon atom ring vertices;

each $R^a$ and $R^b$ is independently selected from the group consisting of hydrogen, hydroxyl, halogen, cyano, $C_{1-8}$ alkyl, $C_{1-8}$ alkoxy, $C_{1-8}$ haloalkyl, $C_{3-6}$ cycloalkyl, $C_{3-6}$ cycloalkylalkyl, amino, $C_{1-8}$ alkylamino, di $C_{1-8}$ alkylamino, carboxamide, carboxy $C_{1-4}$ alkyl ester, carboxylic acid, and —$SO_2$—$C_{1-8}$ alkyl;

or a pharmaceutically acceptable salt thereof.

18. A method in accordance with claim 17 wherein said subject has an inflammatory condition or an immunoregulatory disorder.

19. A method in accordance with claim 17, wherein said subject has a disease or condition selected from the group consisting of transplant rejection, dermatitis, inflammatory bowel disease, asthma, Alzheimer's disease, psoriasis, rheumatoid arthritis, multiple sclerosis, multiple myeloma and osteoporosis.

20. A method in accordance with claim 17, wherein said subject has rheumatoid arthritis.

21. A method in accordance with claim 18, wherein the compound is selected from the group consisting of:

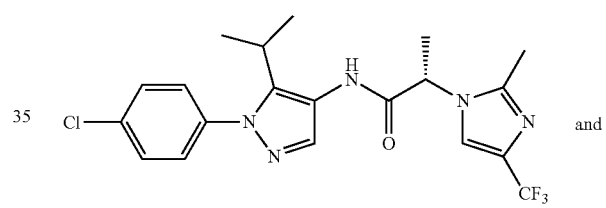

or a pharmaceutically acceptable salt thereof.

22. A method in accordance with claim 19, wherein the compound is selected from the group consisting of:

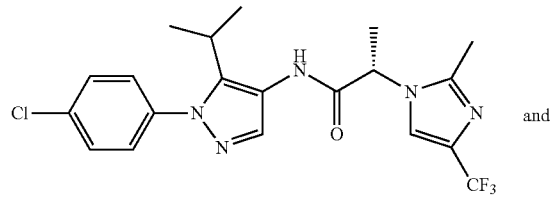

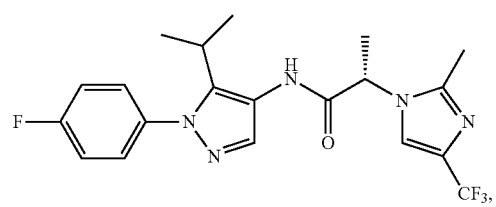

or a pharmaceutically acceptable salt thereof.

23. A method in accordance with claim 20, wherein the compound is selected from the group consisting of:

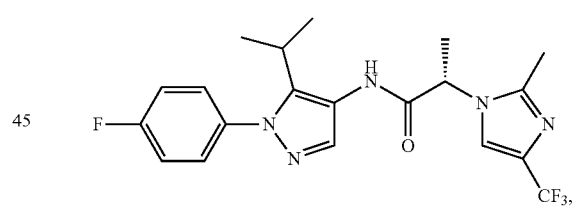

or a pharmaceutically acceptable salt thereof.

* * * * *